US012685298B2

(12) United States Patent
Sullivan et al.

(10) Patent No.: US 12,685,298 B2
(45) Date of Patent: Jul. 21, 2026

(54) SYSTEM AND METHOD FOR INSECT CULTURE MAINTENANCE

(71) Applicant: The Regents of the University of California, Oakland, CA (US)

(72) Inventors: William Sullivan, Santa Cruz, CA (US); Reto Stamm, Santa Cruz, CA (US); Thomas Kornberg, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/746,696

(22) Filed: Jun. 18, 2024

(65) Prior Publication Data

US 2024/0423177 A1     Dec. 26, 2024

Related U.S. Application Data

(60) Provisional application No. 63/587,473, filed on Oct. 3, 2023, provisional application No. 63/522,285, filed on Jun. 21, 2023.

(51) Int. Cl.
*A01K 67/34*          (2025.01)
*A01K 67/362*         (2025.01)

(52) U.S. Cl.
CPC ............ *A01K 67/34* (2025.01); *A01K 67/362* (2025.01)

(58) Field of Classification Search
CPC ........ A01K 67/30; A01K 67/34; A01K 67/36; A01K 67/362; A01K 67/364; A01K 67/366; A01K 67/368; B65D 43/00;

B65D 43/0202; B65D 43/0206; B65D 43/0208; B65D 43/0212; B65D 43/021; B65D 43/0214; B65D 9/711
See application file for complete search history.

(56) References Cited

U.S. PATENT DOCUMENTS 2,144,255 A * 1/1939 Carpenter .............. C12M 23/22
                                                            422/423
2,701,229 A * 2/1955 Scherr .................... C12M 37/02
                                                            220/378

(Continued)

OTHER PUBLICATIONS

Teshler et al., "A Novel Device for the Collection, Storage, Transport, and Delivery of Beneficial Insects, and its Application to Ophraella communa (Coleoptera: Chrysomelidae)", Biocontrol Science and Technology (Jun. 2004) vol. 14, No. 4, pp. 347-357.

*Primary Examiner* — Ebony E Evans
(74) *Attorney, Agent, or Firm* — Carter, DeLuca & Farrell LLP

(57)          ABSTRACT

An insect culture maintenance system includes a vial cap having a top wall and a side wall extending about the top wall that is configured to engage an open end of a vial such that the vial cap is supported on the vial. The side wall of the vial cap defines a tunnel that extends through the side wall. The tunnel is sealed by the vial or by a cap valve supported within the vial cap when the maintenance system is in a first state, and the tunnel is accessible when the maintenance system is in a second state. The vial cap includes a connector that can be coupled to the connector of a second vial cap to couple the first and second vial caps and first and second vials together to allow insects to move from a first vial to a second vial when the tunnels are accessible.

29 Claims, 21 Drawing Sheets

(56)    References Cited

U.S. PATENT DOCUMENTS

| | | | |
|---|---|---|---|
| 3,595,086 A | 7/1971 | Bonnet et al. | |
| 3,687,110 A | 8/1972 | Braunhut | |
| 3,789,799 A | 2/1974 | Orfei | |
| 3,874,335 A | 4/1975 | Galasso | |
| 4,106,438 A | 8/1978 | Nelson | |
| 4,328,636 A | 5/1982 | Johnson | |
| 4,383,385 A * | 5/1983 | Myers | A01K 97/06 |
| | | | 229/5.5 |
| 4,668,633 A * | 5/1987 | Walton | C12M 23/10 |
| | | | 435/305.2 |
| 4,675,298 A * | 6/1987 | Brusewitz | C12M 23/10 |
| | | | 435/801 |
| 4,676,256 A | 6/1987 | Golden | |
| 4,681,220 A * | 7/1987 | Beneke | A01K 97/06 |
| | | | 206/315.11 |
| 4,799,599 A | 1/1989 | Herrmann | |
| 5,348,885 A * | 9/1994 | Labarthe | C12M 23/38 |
| | | | 220/293 |
| 5,731,210 A * | 3/1998 | Rhoades, Jr | B01D 1/00 |
| | | | 34/232 |
| 7,395,623 B2 * | 7/2008 | Park | A01K 1/031 |
| | | | 40/308 |
| D598,738 S * | 8/2009 | Supranowicz | D9/420 |
| 7,935,523 B2 | 5/2011 | Atehortua et al. | |
| 8,420,384 B2 * | 4/2013 | Gazenko | C12M 23/10 |
| | | | 435/305.4 |
| 8,753,325 B2 | 6/2014 | Lev et al. | |
| 9,117,380 B2 * | 8/2015 | Walters | G09F 15/0075 |
| 10,051,845 B1 | 8/2018 | Massaro et al. | |
| 11,814,646 B2 | 11/2023 | Sullivan | |
| 12,004,496 B2 * | 6/2024 | Jansen | A01K 67/30 |
| 12,058,991 B2 * | 8/2024 | McNiel | B65D 43/22 |
| 12,065,670 B2 | 8/2024 | Sullivan | |
| 2009/0030662 A1 | 1/2009 | Guirguis | |
| 2009/0123908 A1 | 5/2009 | Petersson | |
| 2009/0130740 A1 | 5/2009 | Ophardt | |
| 2009/0306621 A1 | 12/2009 | Thome, Jr. et al. | |
| 2013/0153574 A1 * | 6/2013 | Ward | B65D 43/267 |
| | | | 220/839 |
| 2017/0219462 A1 | 8/2017 | Whelan | |
| 2018/0332842 A1 | 11/2018 | Tsao | |
| 2019/0127688 A1 | 5/2019 | Sullivan | |
| 2021/0259306 A1 * | 8/2021 | Goradesky | A24F 9/16 |

* cited by examiner

SYSTEM AND METHOD FOR INSECT CULTURE MAINTENANCE

CROSS-REFERENCE TO RELATED APPLICATIONS

This application claims the benefit of, and priority to, U.S. Provisional Patent Application Ser. No. 63/522,285, filed on Jun. 21, 2023, and U.S. Provisional Patent Application Ser. No. 63/587,473, filed on Oct. 3, 2023. The entire contents of the foregoing applications are incorporated by reference herein.

TECHNICAL FIELD

This disclosure relates generally to systems and methods for maintaining cultures of insects. More specifically, this disclosure relates to systems and methods for maintaining cultures of *Drosophila melanogaster* and other insects.

BACKGROUND

*Drosophila melanogaster*, commonly known as the fruit fly, is a species of fly that is widely used in laboratories for genetic research and instruction. Fruit flies have a life cycle with stages that include egg, larva, pupa, and flying adult. Live cultures of fruit flies are commonly maintained in laboratories in containers with food media placed at the bottom of the containers. Adult fruit flies lay eggs on the food media, and when the eggs hatch, the larvae and pupae feed on the food media. After the fruit flies mature into adults, the adult fruit flies are transferred to a new container with fresh food media. The transfer process involves manual, time-consuming tasks that are performed by laboratory technicians. Errors can result in the escape of adult flies which could compromise experiments. To prevent the escape of adult fruit flies during the transfer process, and to allow examination and sorting of the fruit flies, the fruit flies are often immobilized by chilling or anesthetization. This makes the process even more expensive and time consuming and errors can result in the death of transferred adult flies.

To maintain a healthy culture of fruit flies, the fruit flies are transferred to a new container every 10 to 14 days. Worldwide, it is estimated between 600,000-700,000 stocks must be transferred to new containers manually twice a month. Although robotic systems exist to perform this task, these transfer systems are expensive and not practical for use in small laboratories or for instructional purposes. In addition, manual or robotic transfer as well as typical methods of fly stock storage involving capping tubes with loose fitting cotton or foam stoppers can result in contamination of the cultures with parasites such as mites. Thus, there is a long-standing need for an inexpensive and less labor-intensive system and method for maintaining cultures of fruit flies in the laboratory.

SUMMARY

This disclosure provides a system and method for maintaining cultures of fruit flies and other insects that is simple, inexpensive, and far less labor intensive than existing systems and methods. The disclosed system takes advantage of fundamental differences in behavior and locomotion between the larva and adult insect life cycle stages, and a unique system of connecting containers (e.g., vials). With this new system and method, the need for a technician to transfer each new generation of fruit flies by hand is eliminated, allowing healthy stocks of fruit flies to be more easily maintained for extended periods of time. The system and method allow for separation of distinct generations of fruit flies with minimal effort in a fast and efficient manner while minimizing the likelihood for contamination and mislabeling: well-known issues in stock maintenance.

According to one embodiment of the present disclosure, an insect culture maintenance system is disclosed. The system includes a first cap having a top wall and a side wall extending downward from the top wall. The top wall and the side wall of the first cap define a first cavity that is configured to receive an open end of a first vial. The side wall of the first cap defines a first tunnel and supports a first connector. The first tunnel extends through the side wall of the first cap. The system also includes a second cap having a top wall and a side wall extending downwardly from the top wall. The side wall of the second cap defines a second cavity that is configured to receive an open end of a second vial. The side wall of the second vial defines a second tunnel that extends through the side wall of the second cap. The side wall of the second cap also supports a second connector, where the first connector is couplable to the second connector to releasably secure the first cap to the second cap such that the first tunnel communicates with the second tunnel to allow passage between the first cavity of the first cap and the second cavity of the second cap.

Implementations of the above embodiment may include one or more of the following features. According to one aspect of the above embodiment, the side wall of each of the first cap and second cap may include an inwardly extending rib. The top wall of each of the first cap and the second cap may also include diametrically opposed tabs, each of the diametrically opposed tabs having an overhang that extends over the top wall of the respective first or second cap. The diametrically opposed tabs may be configured to retain a slidable identification tag on at least one of the first cap or the second cap. The top wall of each of the first cap and the second cap may have a raised outer surface. The first connector may also include a first bayonet appendage and a second bayonet appendage positioned on opposite sides of the first tunnel. The second connector may also include a third bayonet appendage and a fourth bayonet appendage positioned on opposite sides of the second tunnel. The first and second bayonet appendages may be configured to rotatably engage with the third and fourth bayonet appendages to couple the first cap to the second cap. The side walls of each of the first cap and the second cap may include a flat surface positioned about the first tunnel and the second tunnel, respectively. The insect culture maintenance system further may include food media positioned within the first and second vials.

According to another embodiment of the present disclosure, a vial cap for insect culture maintenance is disclosed. The vial cap includes a top wall and a side wall extending about the top wall and defining a cap cavity that is configured to receive an open end of a vial such that the vial cap is slidable along an outer surface of the vial between a closed position and an open position. The side wall defines a tunnel that extends through the side wall. The tunnel is sealed by the vial when the vial cap is in the closed position and is unobstructed by the vial when the vial cap is in the open position. The vial cap also includes a connector supported on the side wall. The connector is configured to couple the vial cap to a second vial cap.

Implementations of the above embodiment may include one or more of the following features. According to one aspect of the above embodiment, the side wall may include an inwardly extending rib configured to engage an outwardly extending rib of the vial when the vial cap is in the open position to releasably retain the vial cap on the vial. The top wall may include diametrically opposed tabs, each of the diametrically opposed tabs having an overhang that extends over the top wall. The diametrically opposed tabs may be configured to retain a slidable identification tag on the vial cap. The top wall may have a raised outer surface that is angled upwardly from side edges towards a center of the top wall. The connector may include a first bayonet appendage and a second bayonet appendage positioned on opposite sides of the tunnel. The side wall may include a flat surface positioned about the tunnel.

According to a further embodiment of the present disclosure, a method of maintaining an insect culture is disclosed. The method includes positioning a first vial and cap assembly having an insect culture disposed inside a first vial of the first vial and cap assembly adjacent a second vial and cap assembly having a food media received within a second vial of the second vial and cap assembly. The method also includes placing a first cap of the first vial and cap assembly and a second cap of the second vial and cap assembly in a coupled configuration such that a first tunnel defined by the first cap communicates with a second tunnel defined by the second cap. The method further includes moving the first cap and the second cap while in the coupled configuration in relation to the first vial and the second vial, respectively, to open the first tunnel and the second tunnel such that a first cavity of the first vial communicates with a second cavity of the second vial through the first tunnel and the second tunnel.

Implementations of the above embodiment may include one or more of the following features. According to one aspect of the above embodiment, placing the first cap and the second cap in the coupled configuration may include rotating the first vial and cap assembly in relation to the second vial and cap assembly to connect first bayonet appendages of the first vial and cap assembly with second bayonet appendages of the second vial and cap assembly. The method also may include sliding an identification tag beneath first tabs supported on the first vial and cap assembly to a position beneath second tabs supported on the second vial and cap assembly after the first cap is coupled to the second cap. The method may further include moving the first cap and the second cap while in the coupled configuration in relation to the first vial and to the second vial, respectively, to close the first tunnel and the second tunnel. The method may additionally include rotating in a second direction, opposite the first direction, the first cap of the first vial and cap assembly in relation to the second cap of the second vial and cap assembly to uncouple the first cap from the second cap.

According to yet another embodiment of the present disclosure, an insect culture maintenance system is disclosed. The insect culture maintenance system includes a cap having a top wall and a side wall extending downwardly from the top wall. The top wall and the side wall define a first cavity and the side wall defines a tunnel and a through bore that extend through the side wall. The system also includes a cap valve having a body and includes an abutment member extending outwardly from the body through the through bore of the cap. The body of the cap valve is movable from a first state to a second state in response to inward movement of the abutment member within the through bore of the cap, where in the first state, the cap valve seals the tunnel, and in the second state, the cap valve unseals the tunnel.

Implementations of the above embodiment may include one or more of the following features. According to one aspect of the above embodiment, the insect culture maintenance system may further include a vial having an outer surface, a closed end, and an open end. The vial defines a second cavity and the open end of the vial defines an opening that provides access to the second cavity. The side wall of the cap may be received within the open end of the vial. The side wall of the cap may support gripping members positioned to engage the outer surface of the vial to secure the cap to the vial. The vial may include a rib that is positioned adjacent the open end of the vial, and the gripping members may include detents that engage the rib. The body of the cap valve may be formed from a resilient material, and the side wall of the cap may include an inner surface. The cap valve has a seal portion that is engaged with the inner surface of the side wall of the cap to seal the tunnel when the cap valve is in the first state. The inward movement of the abutment member within the through bore of the cap deforms the body of the cap valve to move the seal portion of the cap valve away from the inner surface of the side wall of the cap to unseal the tunnel. The top wall supports diametrically opposed tabs, each of the diametrically opposed tabs having an overhang that extends over the top wall, such that the diametrically opposed tabs retain a slidable identification tag on the cap.

According to a further embodiment of the present disclosure, an insect culture maintenance system is disclosed. The insect culture maintenance system includes a first cap assembly having a first cap, which has a top wall and a side wall extending downwardly from the top wall. The top wall and the side wall of the first cap define a first cavity and the side wall of the first cap defines a first tunnel and a through bore that extend through the side wall of the first cap. The side wall of the first cap also has an outer surface supporting a first connector. The first cap assembly also includes a first cap valve having a body and including a first abutment member extending outwardly from the body through the first through bore of the first cap. The body of the first cap valve is movable from a first state to a second state in response to inward movement of the abutment member within the first through bore of the cap, where in the first state, the first cap valve seals the first tunnel, and in the second state, the first cap valve unseals the first tunnel.

The system further includes a second cap assembly having a second cap, which has a top wall and a side wall extending downwardly from the top wall. The top wall and the side wall of the second cap define a second cavity configured to receive an open end of a second vial. The side wall of the second cap defines a second tunnel and a second through bore that extend through the side wall of the second cap. The side wall of the second cap also has an outer surface supporting a second connector. The second cap assembly also includes a second cap valve having a body and includes a second abutment member extending outwardly from the body through the through bore of the second cap. The body of the second cap valve is movable from a first state to a second state in response to inward movement of the second abutment member within the second through bore of the second cap, where in the first state of the second cap valve, the second cap valve seals the second tunnel, and in the second state of the second cap valve, the second cap valve unseals the second tunnel. Additionally, the first connector is couplable to the second connector to secure the first cap to the second cap.

Implementations of the above embodiment may include one or more of the following features. According to one aspect of the above embodiment, the first cap may be positioned to engage the second abutment member and the second cap may be positioned to engage the first abutment member when the first connector is coupled to the second connector to move the first abutment member and the second abutment member inwardly within the first through bore and the second through bore. The insect culture maintenance system may further include a first vial and a second vial, each of the first vial and the second vial includes an open end and a closed end. The first vial defines a third cavity and the second vial defines a fourth cavity. The first cap may be supported on the open end of the first vial and the second cap may be supported on the open end of the second vial. The side wall of the first cap may be received within the third cavity of the first vial and the side wall of the second cap may be received within the fourth cavity of the second vial. The bodies of the first cap valve and the second cap valve may be formed from a resilient material, and the side walls of the first cap and the second cap may include an inner surfaces. The first cap valve and the second cap valve may have seal portions that are engaged with the inner surfaces of the side walls of the first cap and the second cap to seal the tunnels when the first cap valve and the second cap valve are in the first states. Inward movements of the first abutment member and the second abutment member within the first through bore and the second through bore of the first cap and the second cap may deform the bodies of the first cap valve and the second cap valve to move the seal portions of the first cap valve and the second cap valve away from the inner surfaces of the side walls of the first cap and the second cap to unseal the first tunnel and the second tunnel. The side walls of the first cap and the second cap may support gripping members positioned to engage the outer surfaces of the first vial and the second vial to secure the first cap and the second cap to the first vial and the second vial. Each of the first vial and the second vial may include a rib that is positioned adjacent the open end of the first vial and the second vial, and the gripping members may include detents that engage the ribs. The top walls of the first cap and the second cap support diametrically opposed tabs, each of the diametrically opposed tabs having an overhang that extends over the top wall. The diametrically opposed tabs may retain a slidable identification tag on the first cap and the second cap.

BRIEF DESCRIPTION OF DRAWINGS

Various aspects of the disclosed systems and methods for maintaining cultures of fruit flies and other insects are described herein below with reference to the drawings, wherein.

DETAILED DESCRIPTION

Figure 1:
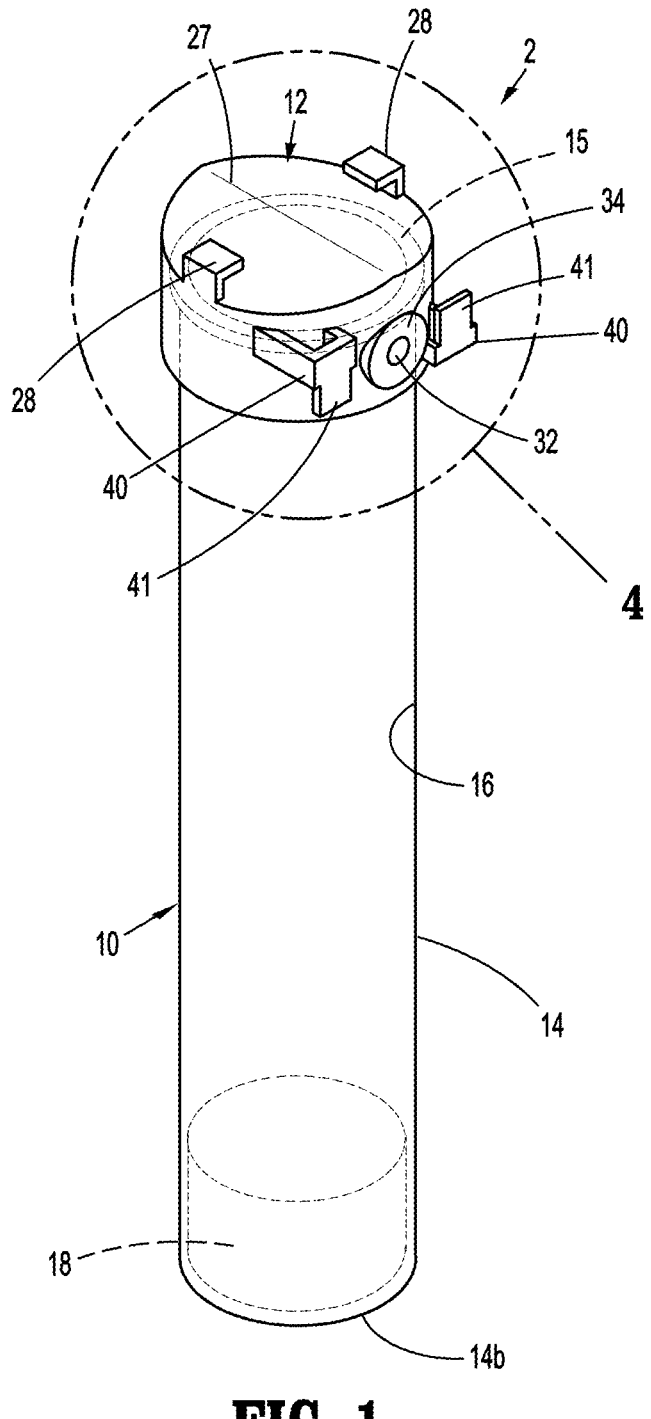
FIG. 1 is a side perspective view of a first vial and cap assembly including a first vial and a first vial cap of the disclosed system and method for insect culture maintenance with the first vial cap coupled to the first vial in a closed position according to an embodiment of the present disclosure.

The disclosed system and method for maintaining cultures of fruit flies and other insects will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Figures 2, 3:
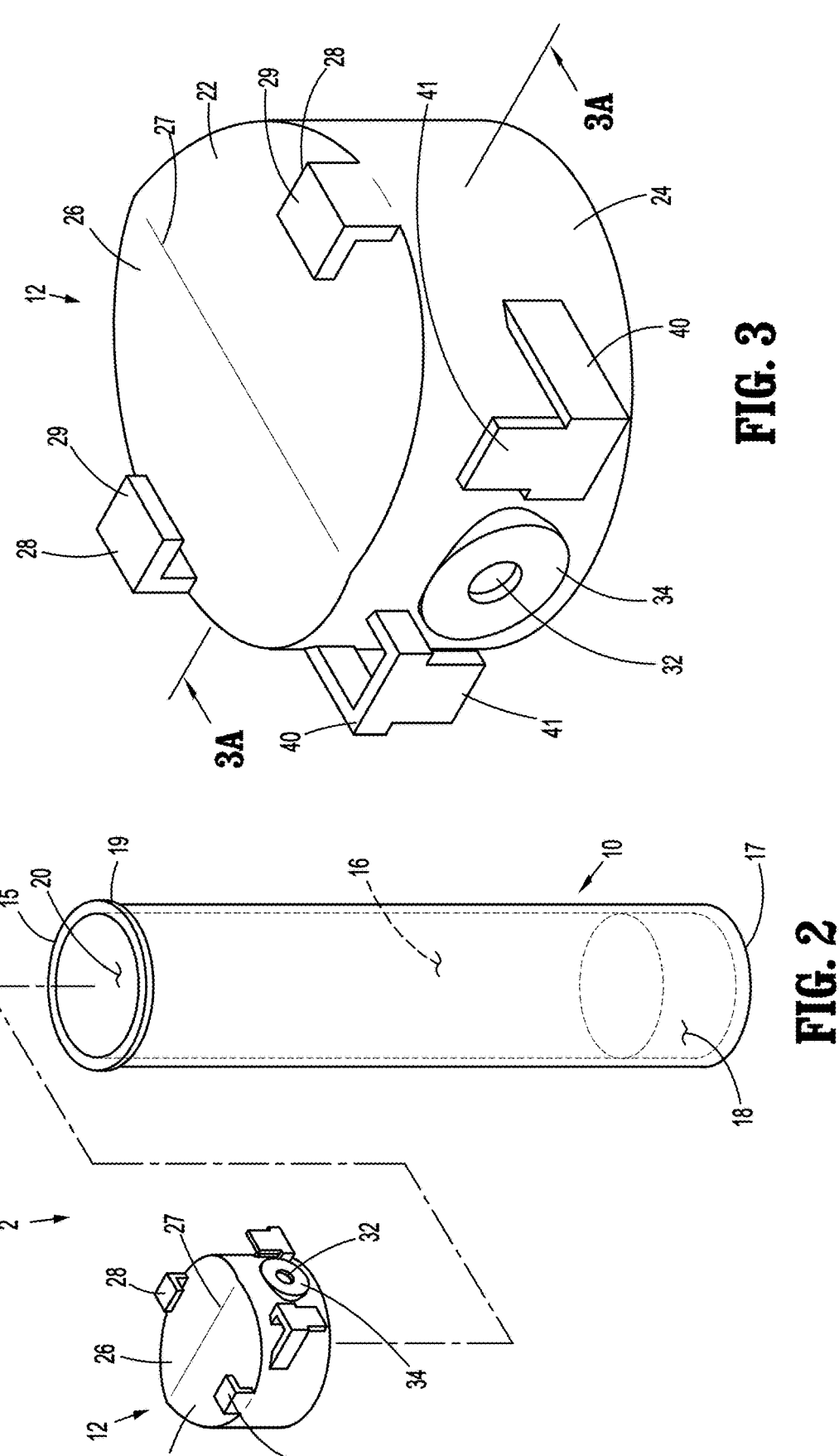
FIG. 2 is a side perspective view of the first vial and cap assembly shown in FIG. 1 with the first vial cap separated from the first vial.
FIG. 3 is an enlarged, side perspective view of the first vial cap shown in FIG. 2.

FIGS. 1 and 2 illustrate a first vial and cap assembly of the disclosed system and method for maintaining cultures of fruit flies and other insects shown generally as first vial and cap assembly 2. The first vial and cap assembly 2 includes a first vial 10 and a first vial cap 12. The first vial 10 is illustrated as having a cylindrical body 14 with an open end 15 and a closed end 17. It is envisioned that the first vial 10 need not be cylindrical but rather can have a variety of configurations including square, rectangular, hexagonal, octagonal, oval or the like and the first vial cap 12 can have a corresponding shape to engage the first vial 10 in the manner described below.

The body 14 of the first vial 10 defines a cavity 16 that receives a food media 18 for nourishing an insect culture that is supported within the cavity 16, i.e., in the closed end 17 of the body 14 of the first vial 10. The food media 18 can be placed within the cavity 16 through an opening 20 defined by the open end 15 of the body 14. The body 14 of the vial 10 also includes an annular rib 19 that is formed on the open end 15 of the vial 10 and extends about the opening 20.

Figures 3A, 4:
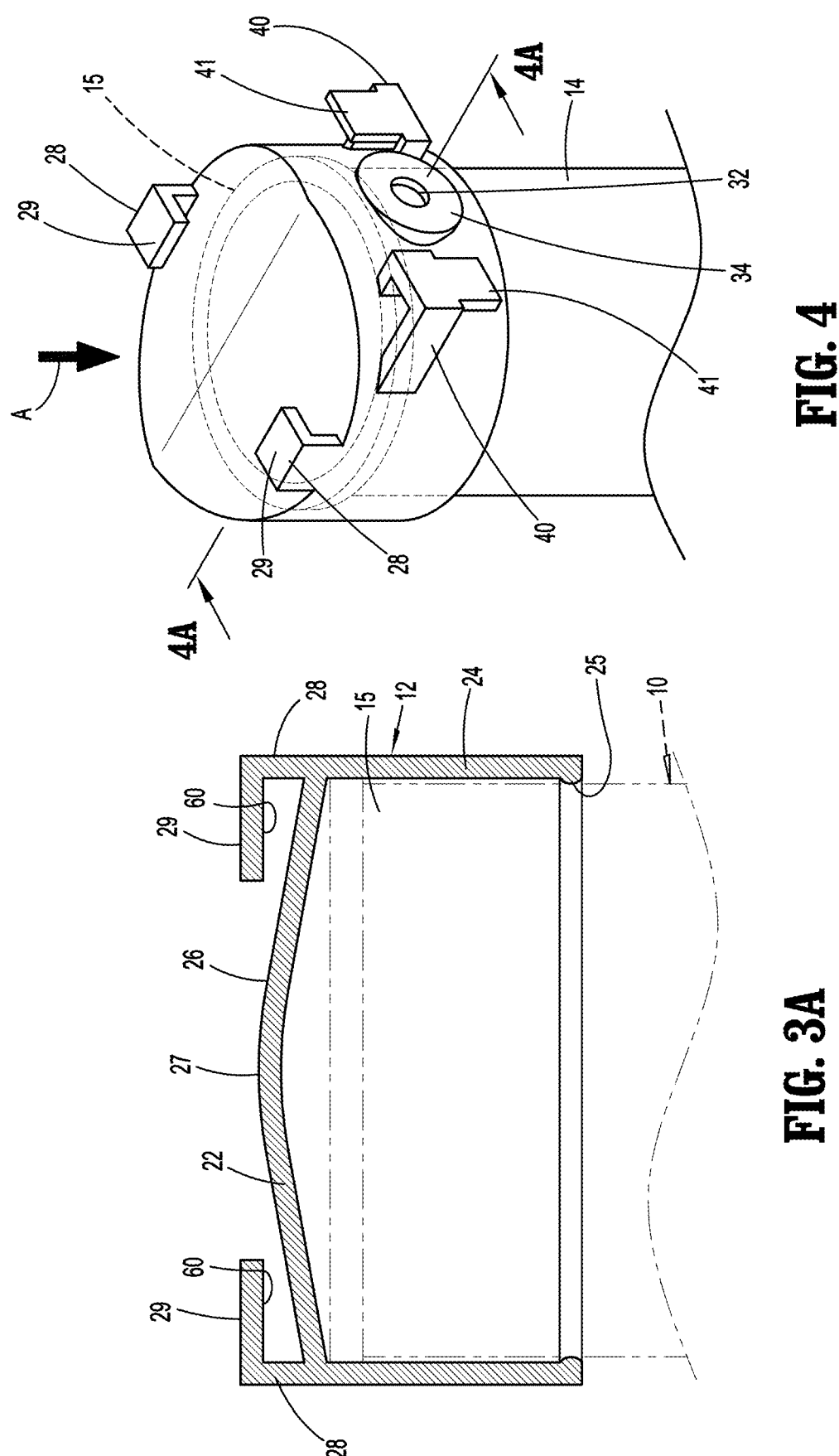
FIG. 3A is a cross-sectional view taken along section line 3A-3A of the first vial cap 2.
FIG. 4 is an enlarged view of the indicated area of detail shown in FIG. 1 with the first vial shown partly in phantom and the first vial cap coupled to the first vial in the closed position.

FIGS. 3 and 3A illustrate the first vial cap 12, which includes a top wall 22 and a side wall 24 that has a configuration that corresponds to the configuration of the open end 15 of the first vial 10, e.g., cylindrical, square, oval, hexagonal, octagonal, etc. In aspects of the disclosure, the top wall 22 of the first vial cap includes an outer raised surface 26 that is angled or sloped upwardly from side edges of the first vial cap 12 towards a protrusion 27 of the first vial cap 12. The protrusion 27 may be a ridge, a peak, a curved surface, or any other surface feature. In embodiments, the raised surface 26 may have a dome shape. The top wall 22 may also have one or more air openings sized to prevent escape of the insects held in the first vial 10 while allowing for gas exchange for the cavity 16.

The top wall 22 of the first vial cap 12 also supports diametrically disposed tabs 28 that are positioned on opposite sides of the top wall 22. In aspects of the disclosure, the tabs 28 have L-shaped configurations that include overhangs 29 that extend over the outer surface 26 of the top wall 22 of the first vial cap 12. The tabs 28 are provided to secure an identification tag 100 (FIG. 9) to the first vial cap 12 as described in further detail below. The overhangs 29 of the tabs 28 define a channel that slidably receives the identification tag 100 to allow the identification tag 100 to slide onto and off the outer surface 26 of the top wall 22 of the first vial cap 12. The raised surface 26 increases frictional engagement between the top wall 22 of the first vial cap 12 and the bottom surface of the identification tag 100 to secure the identification tag 100 to the first vial cap 12.

The side wall 24 of the first vial cap 12 is received about the open end 15 of the vial 10 and is in frictional engagement such that the first vial cap 12 can slide along the outer surface of the first vial 10 between an open position and a closed position. The first vial cap 12 is fitted tightly about the vial 10, which prevents invasion of the stocks by mites and other parasites, while allowing for sliding of the first vial cap 12 along the vial 10. The side wall 24 of the vial cap 12 also defines a tunnel 32 that extends through the side wall 24 of the vial cap 12 and provides a pathway from within the cavity 16 of the first vial 10 when the first vial cap 12 is in the open position. In the open position, the tunnel 32 is lifted at least partially above a plane defined by the open end 15 of the vial 10 such that the tunnel 32 is in communication with the cavity 16. In the closed position the tunnel 32 is below the plane defined by the open end 15 of the vial 10 such that the access to the cavity 16 from the tunnel 32 is blocked. The side wall 24 of the vial cap 12 further includes an inner surface that has an inwardly extending annular rib 25 (FIG. 3A) that is positioned to engage the annular rib 19 of the first vial 10 when the first vial cap 12 is in the open position. Engagement between the annular rib 19 and the annular rib 25 prevents unintentional separation of the first vial cap 12 from the first vial 10.

The annular rib 25 of the first vial cap 12 may be continuous as shown or can be segmented (i.e., including a plurality of segments separated by gaps). The segments and the gaps may be of the same or varying lengths, such that the segments are evenly spaced. In embodiments, the annular rib 25 may have 2-16 segments and corresponding number of gaps. The gaps make it easier to seat the first vial cap 12 on the first vial 10 as the annular rib 25 catches the annular rib 19 on one side. In particular, the gaps allow the first vial cap 12 to slide on the first vial 10 sideways and pop down one side, without the first vial cap 12 escaping and slipping away.

In aspects of the disclosure, the side wall 24 of the vial cap 12 defines a flat surface 34 that is formed about the tunnel 32. The flat surface 34 is provided to locate or position the first vial cap 12 in relation to a second vial cap 12a (FIG. 7) that is to be coupled to the first vial cap 12 to align the tunnels 32 of the first vial cap 12 with a tunnel 32a of a second vial cap 12a (FIG. 7C) when the first and second vial caps 12, 12a are coupled together as described below.

The first vial cap 12 includes connectors 40 that depend from the side wall 24 of the vial cap 12. In aspects of the disclosure, the connectors 40 are configured to engage connectors 40a of the second vial cap 12a (FIG. 7A) to releasably secure the first and second vial caps 12, 12a together. In certain aspects of the disclosure, the connectors 40 are bayonet appendages 41 that can be rotated into engagement with correspondingly configured connectors 40a of the second vial cap 12a to secure the first and second vial caps 12, 12a together.

It is envisioned that the connectors 40, 40a of the first and second vial caps 12, 12a can have a variety of different configurations capable of releasably securing the first and second vial caps 12, 12a together. For example, the connectors 40, 40a can include interlocking features, e.g., dove-tail connectors, to secure the vial caps 12, 12a together. It is noted that if the connectors 40, 40a are dove-tail connectors, the connectors 40, 40a would slide linearly in relation to each other to secure the first and second vial caps 12, 12a together.

Figure 4A:
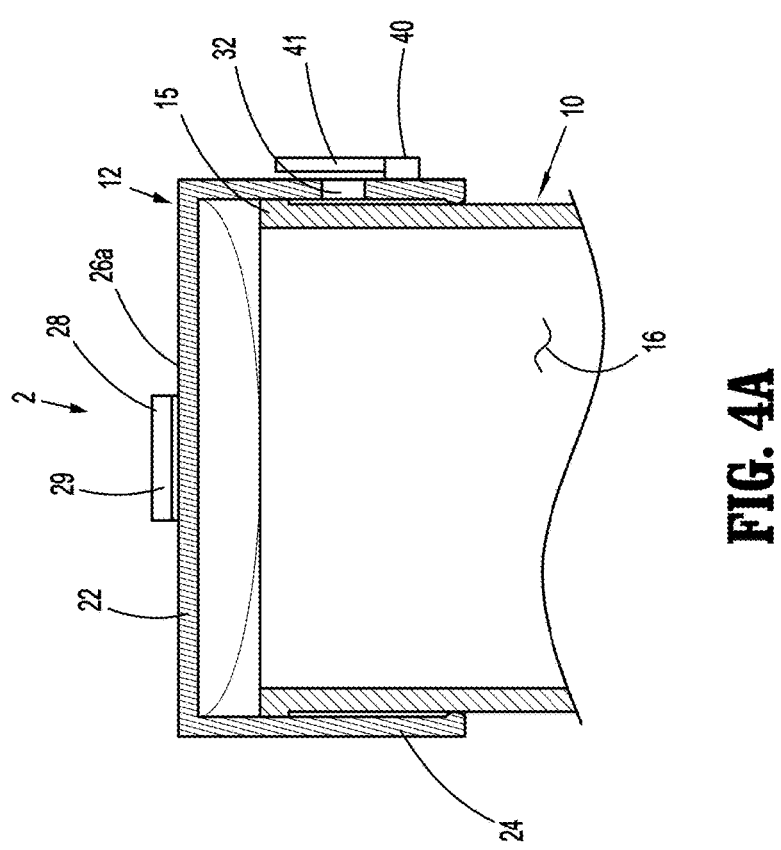
FIG. 4A is a cross-sectional view taken along section line 4A-4A of FIG. 4.

FIGS. 4 and 4A illustrate the first vial and cap assembly 2 with the first vial cap 12 positioned on the first vial 10 in the closed position. As described above, the first vial cap 12 is slidably received about the open end 15 of the first vial 10 and is movable between an open position and a closed position. When the first vial cap 12 is slid about the first vial 10 downwardly in the direction indicated by arrow "A" in FIG. 4 to the closed position, the tunnel 32 in the side wall 24 of the first vial cap 12 is sealed by the first vial 10 thereby sealing the cavity 16 of the first vial 10.

Figure 5:
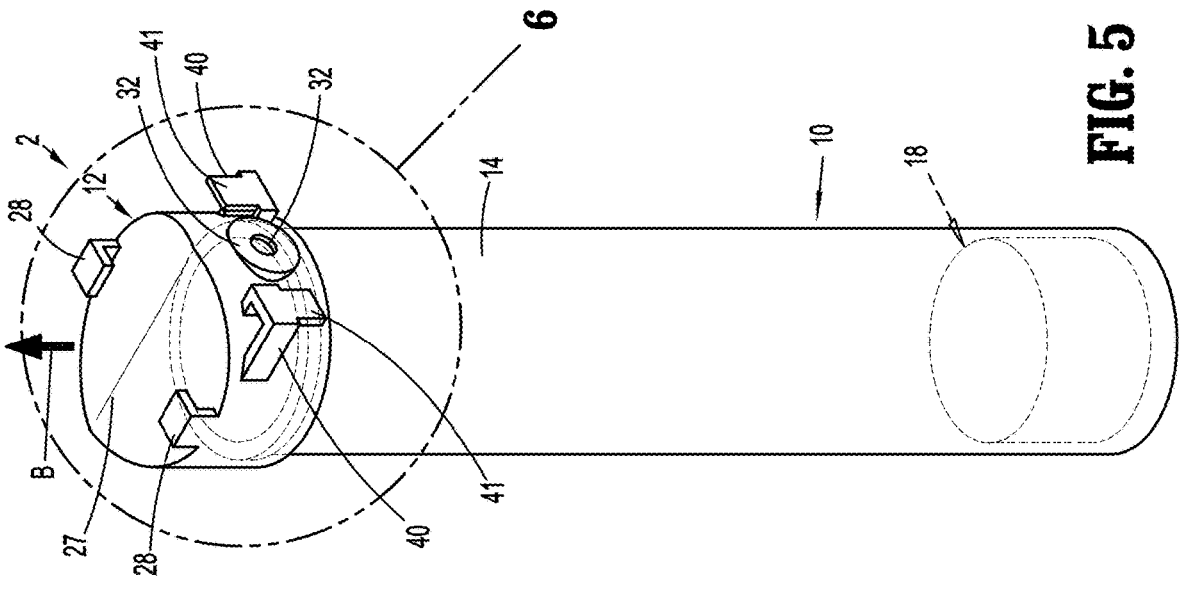
FIG. 5 is a side perspective view of the upper portion of the first vial and cap assembly shown in FIG. 1 with the first vial shown partly in phantom and the first vial cap coupled to the first vial in an open position.
Figures 6, 6A:
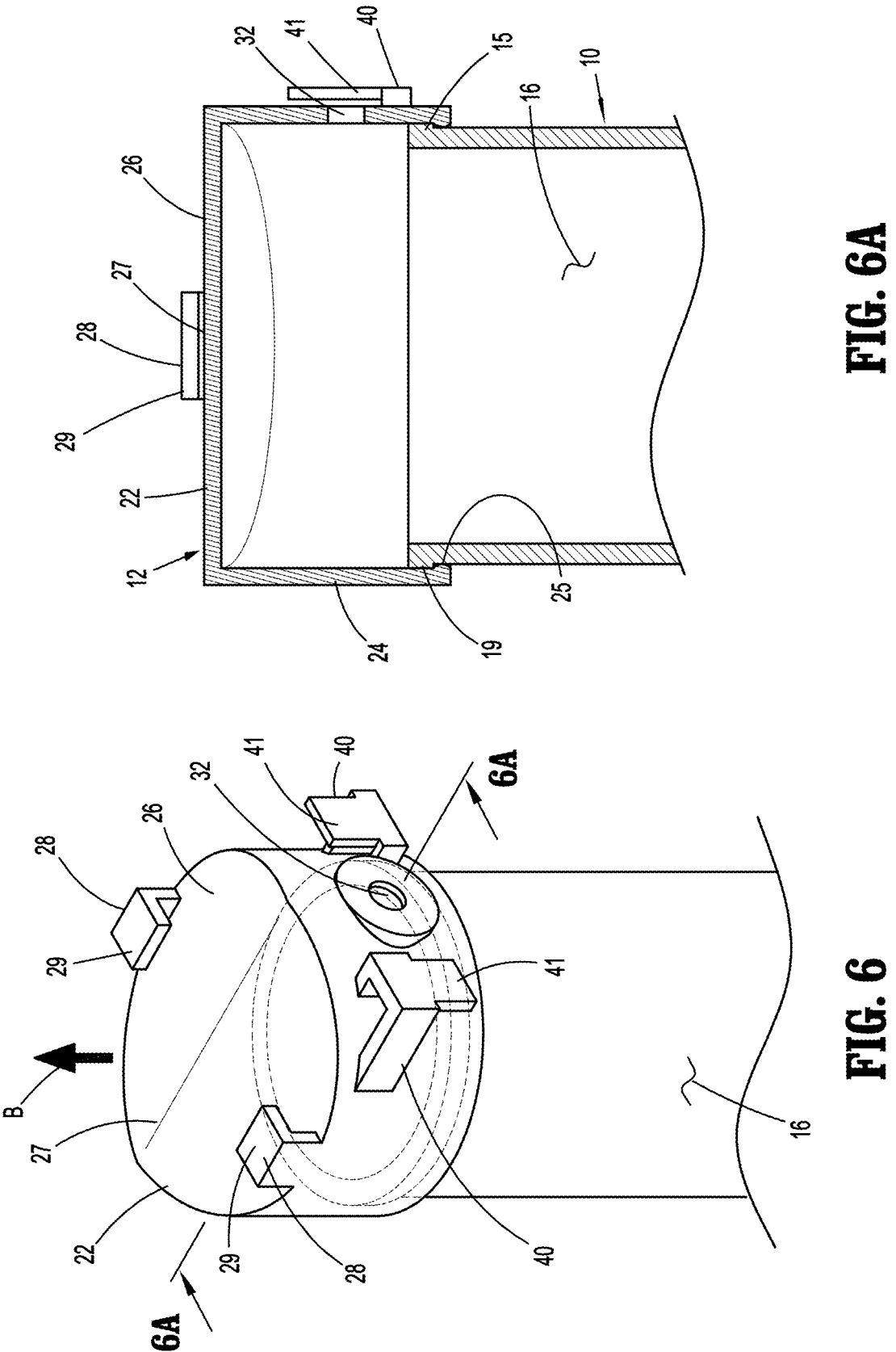
FIG. 6 is an enlarged view of the indicated area of detail shown in FIG. 5.
FIG. 6A is a cross-sectional view taken along section line 6A-6A of FIG. 6.

FIGS. 5 to 6A illustrate the first vial and cap assembly 2 with the first vial cap 12 moved in relation to the first vial 10 from the closed position to the open position. When the vial cap 12 is slid upwardly about the vial 10 in the direction indicated by arrow "B" in FIGS. 5 and 6 from the closed position to the open position, the tunnel 32 in the side wall 24 of the first vial cap 12 moves to a position above the open end 15 of the first vial 10 to provide a pathway through the first vial cap 12 from within the cavity 16 of the first vial 10. When the vial cap 12 is in the open position, the annular rib 25 of the first vial cap 12 is engaged with the annular rib 19 of the first vial 10 (FIG. 6) to prevent inadvertent separation of the first vial cap 12 from the first vial 10. It is noted that the vial cap 12 can be formed from a deformable material, which may be any suitable polymer, to facilitate separation of the first vial cap 12 from the first vial 10 upon application of a predetermined force in the direction of arrow "B" to the first vial cap 12. The first vial cap 12 may be constructed using any suitable manufacturing technique such as subtractive manufacturing (e.g., computer numerical control (CNC) milling, machining, laser cutting), additive manufacturing (e.g., 3D printing), injection molding, thermal or ultrasonic welding of walls, and the like. It is also envisioned that the first vial 10 can be formed from a variety of different rigid or deformable materials including glass and a variety of plastic materials.

Figure 7:
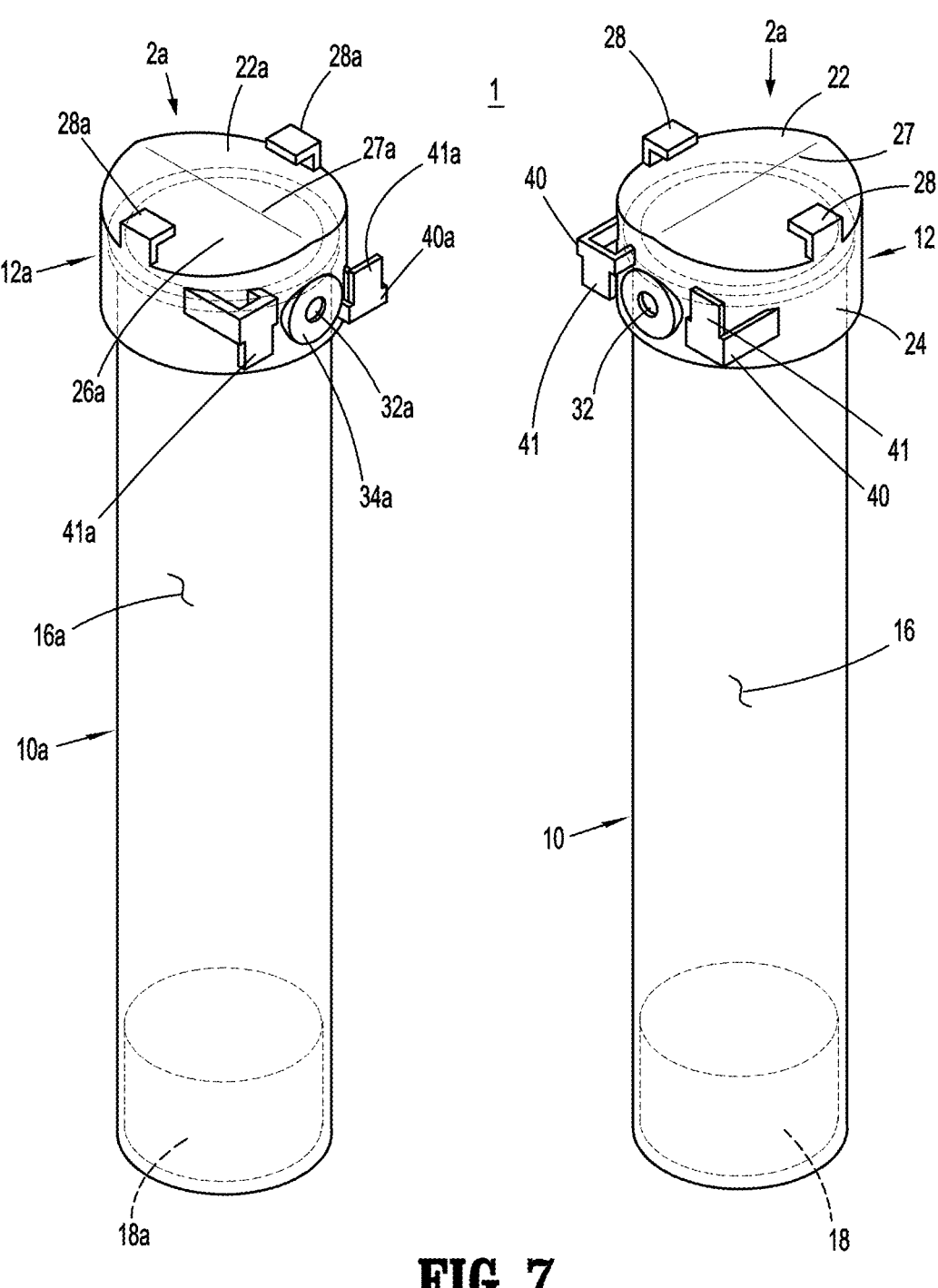
FIG. 7 is a side perspective view of the first and second vial and cap assemblies prior to coupling of the first vial and cap assembly with the second vial and cap assembly.

FIG. 7 illustrates the first vial and cap assembly 2 in association with a second vial and cap assembly 2a. The second vial and cap assembly 2a is substantially identical to the first vial and cap assembly 2 and includes a second vial 10a and a second vial cap 12a. The second vial cap 12a is substantially identical to the first vial cap 12 and includes a top wall 22a that has an outer surface 26a that includes a protrusion 27a and supports tabs 28a, and a side wall 22a that defines a tunnel 32a and supports connectors 40a. The connectors 40a are configured to releasably engage the connectors 40 of the first vial cap 12 to secure the first and second vial caps 12, 12a together such that the tunnel 32 of the first vial cap 12 is aligned with the tunnel 32a of the second vial cap 12a. The side wall 22a of the second vial cap 12a also defines a flat surface 34a that can be pressed against the flat surface 34 of the first vial cap 12 when the vial caps 12, 12a are coupled together to align the tunnels 32, 32a of the first and second vial caps 12, 12a.

Figure 7A:
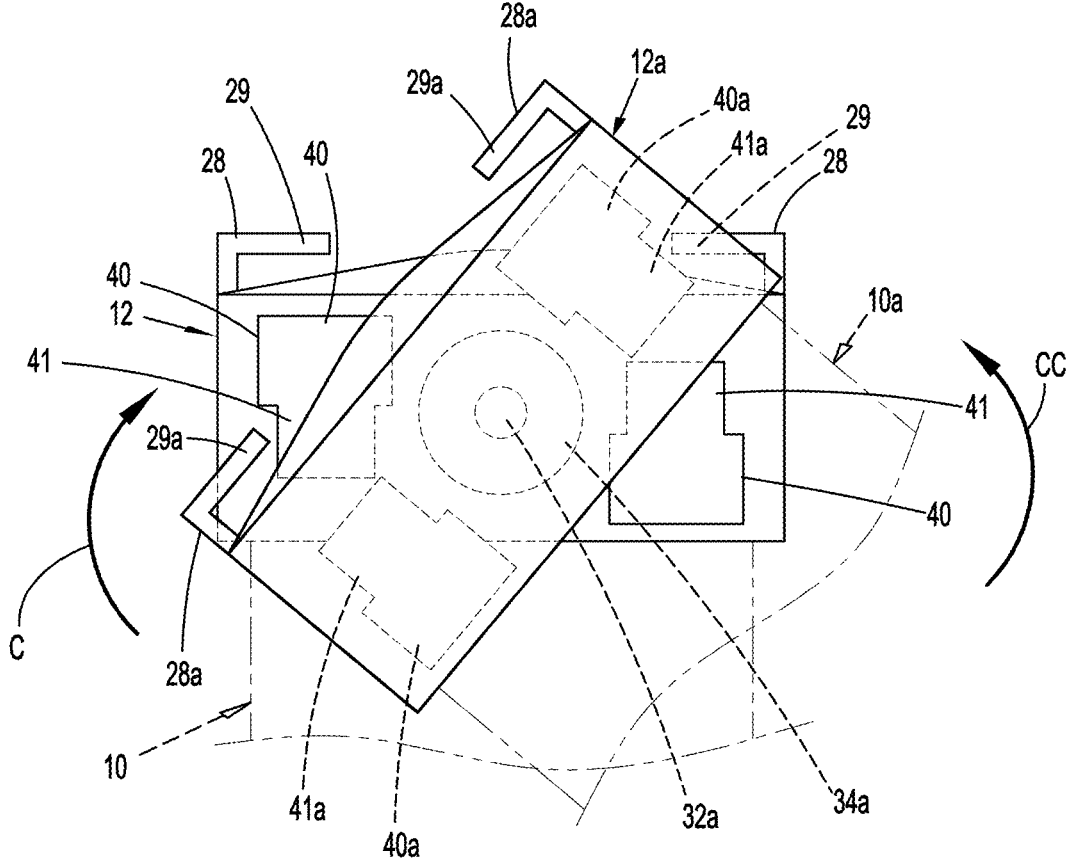
FIG. 7A is a side perspective cutaway view shown partly in phantom of the first vial and cap assembly being coupled to the second vial and cap assembly.
Figure 7B:
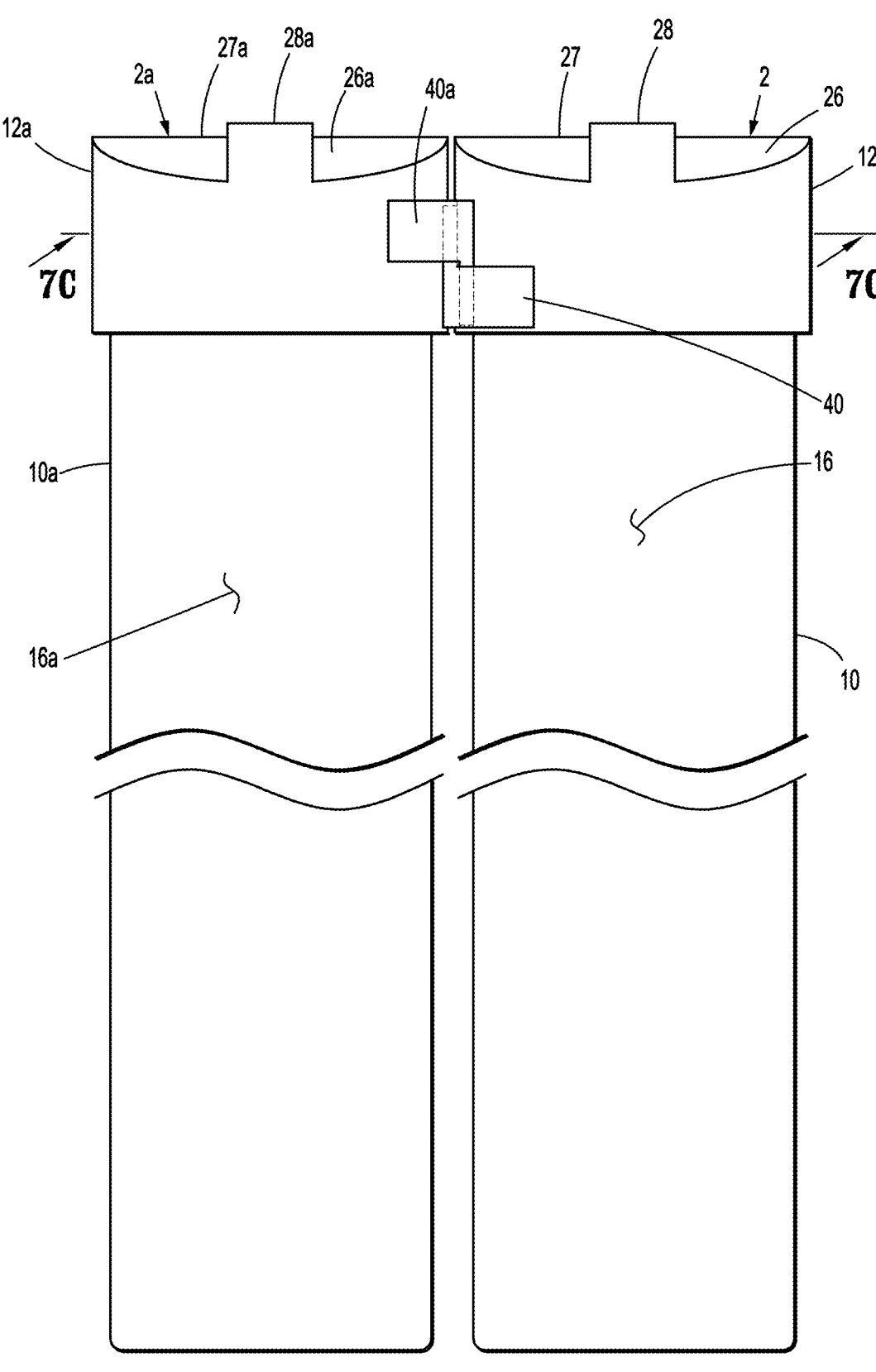
FIG. 7B is a side view of the first and second vial and cap assemblies coupled together in a coupled configuration.
Figure 7C:
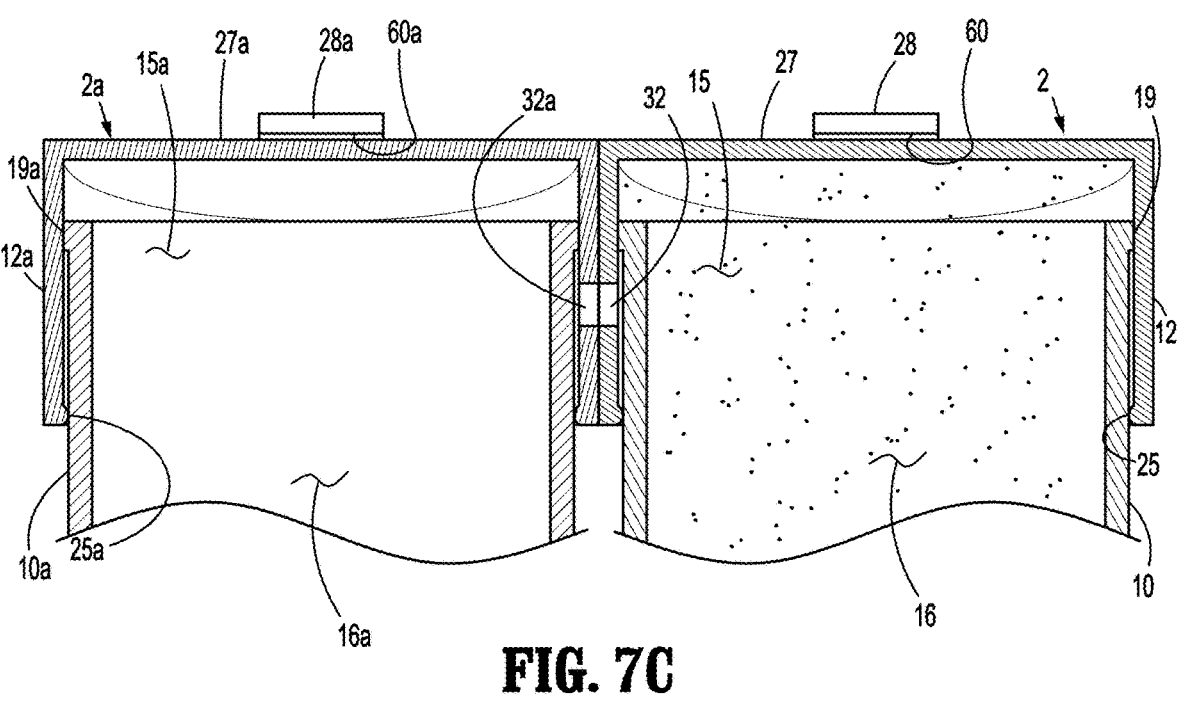
FIG. 7C is a cross-sectional view taken along section line 7C-7C of FIG. 7B illustrating the first and second vial and cap assemblies in the closed positions.

FIGS. 7A-7C illustrate the system 1 for maintaining cultures the first and second vial and cap assemblies 2, 2a as the assemblies 2, 2a are coupled together. To couple the second vial and cap assembly 2a to the first vial and cap assembly 2, the flat surfaces 34 and 34a of the first and second vial caps 12, 12a are pressed into engagement with each other with the connectors 40, 40a of the first and second vial caps 12, 12a rotatably offset from each other. Next, the second vial and cap assembly 12a is rotated in relation to the first vial and cap assembly 12 in the direction indicated by arrow "C" in FIG. 7A such that the bayonet appendages 41a of the second vial cap 12a move into engagement with the bayonet appendages 41 of the first vial cap 12 to secure the first and second vial and cap assemblies 2, 2a together. When the vial caps 12, 12a are properly coupled to each other, the tunnel 32 of the first vial cap 12 is aligned with the tunnel 32a of the second vial cap 12a. It is noted that the vial and cap assemblies 2, 2a can be uncoupled by rotating the second vial and cap assembly 2a in relation to the first vial and cap assembly 2 in the direction indicated by an arrow "CC", which is opposite to the direction indicated by arrow "C", to disengage the bayonet appendages 41 from the bayonet appendages 41a.

Figure 8:
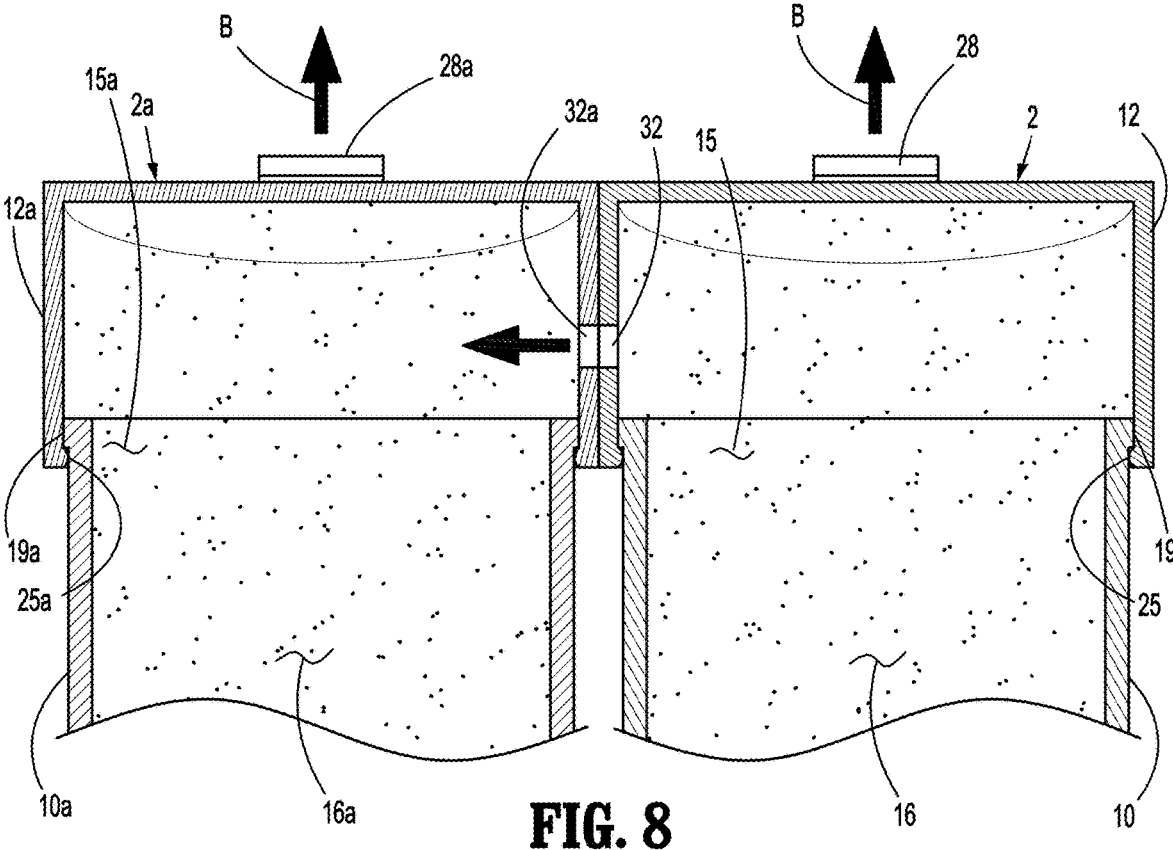
FIG. 8 is a cross-sectional view taken of the upper portions of the first and second vial and cap assemblies shown in FIG. 7B in the open positions.

Typically, when the first and second vial and cap assemblies 2, 2a are coupled together, the vial caps 12, 12a are in the closed positions on the vials 10, 10a (FIG. 7C) such that there is no communication between the cavity 16 of the first vial 12 and the cavity 16a of the second vial 12a. Thus, in the closed position, each of the first and second vials 10, 10a are enclosed and sealed from the surrounding environment. Once the first vial and cap assembly 2 is coupled to the second vial and cap assembly 2a, the first and second vial caps 12, 12a can be moved from the closed positions (FIG. 7) to the open positions (FIG. 8). This is accomplished by moving the first and second vial caps 12, 12a upwardly (as viewed in FIG. 8) in the direction of arrow "B" in FIG. 8 to move the tunnels 32, 32a upwardly past the open ends 15, 15a of the first and second vials 10, 10a. When the first and second vial caps 12, 12a are in the open positions, the cavity 16 of the first vial 10 communicates with the cavity 16a of the second vial 10a through the channel created by the tunnels 32, 32a. Where insects are positioned within the cavity 16 of the first vial 10, the insects can now pass through the tunnels 32, 32a and travel from the cavity 16 of the first vial 10 into the cavity 16a of the second vial 10a.

Figures 9, 10:
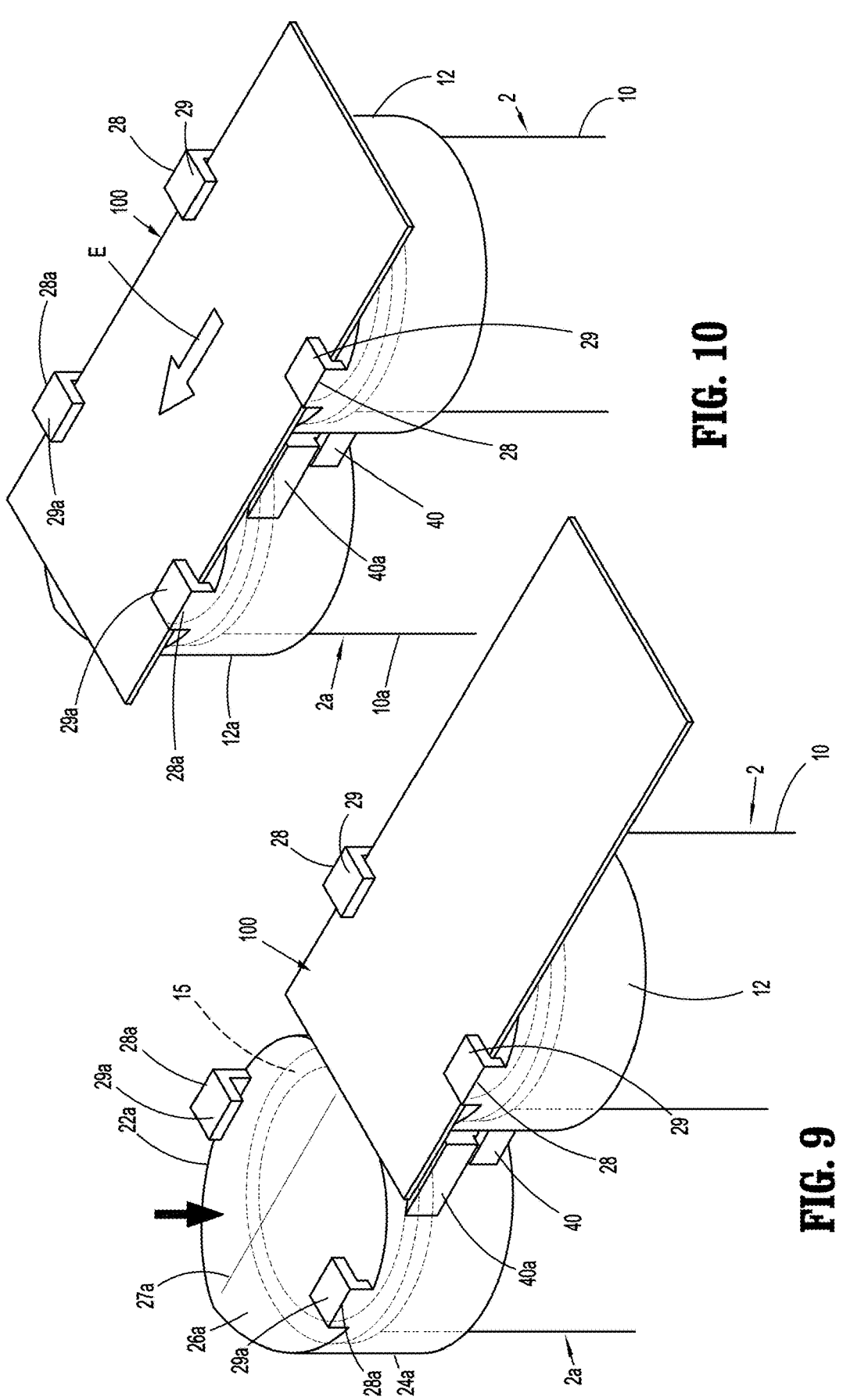
FIG. 9 is a side perspective view of the upper portions of the first and second vial and cap assemblies including an identification tag positioned on the first vial and cap assembly.
FIG. 10 is a side perspective view of the upper portions of the first and second vial and cap assemblies with the identification tag positioned on the first and second vial and cap assemblies.
Figure 11:
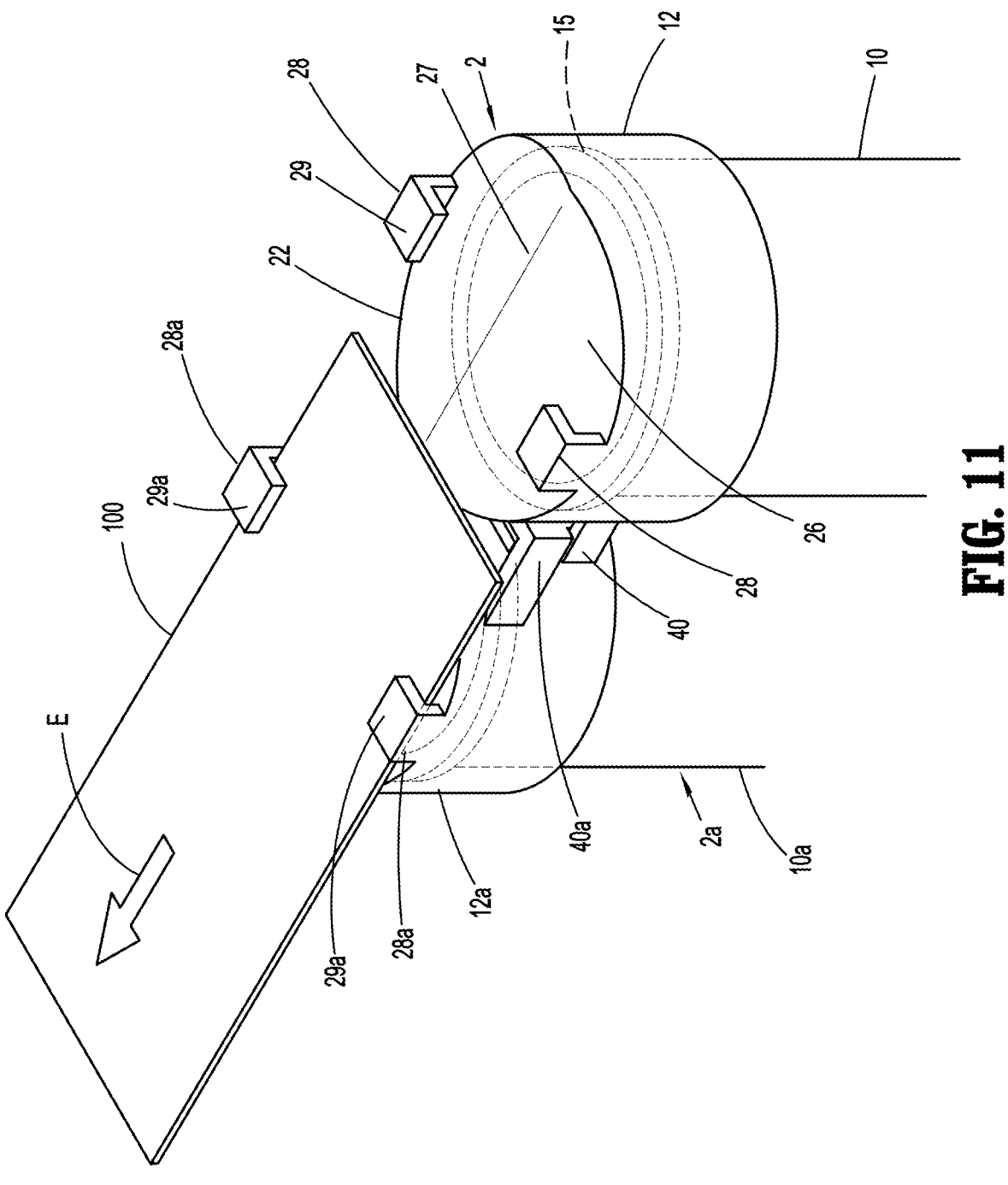
FIG. 11 is a side perspective view of the upper portions of the first and second vial and cap assemblies with the identification tag positioned on the second vial and cap assembly.

FIGS. 9-11 illustrate the first and second vial and cap assemblies 2, 2a with an identification tag 100 attached to one or both of the first or second vial caps 12, 12a. The identification tag 100 may be any rigid or semi rigid substrate, e.g., cardboard, plastic frame, etc. including a readable identifier. As described above, each of the vial caps 12, 12a includes tabs 28, 28a that include overhangs 29, 29a, respectively, that extend over the outer surfaces 26, 26a of the vial caps 12, 12a. The tabs 28, 28a are positioned on opposite sides of the vial cap 12, 12a such that the protrusions 27, 27a are positioned between the tabs 28, 28a on each of the vial caps 12, 12a, respectively. In aspects of the disclosure, the tabs 28, 28a have a lower surface 60, 60a (FIG. 3A) that is positioned in a plane slightly above the protrusions 27, 27a. When the identification tag 100 is slid under the overhangs 29, 29a, the lower surfaces 60, 60a of the tabs 28, 28a press the identification tag 100 against the outer surfaces 26, 26a of the vial caps 12, 12a to releasably secure the identification tags 100 to the vial caps 12, 12a. The identification tag 100 can be easily slid beneath the tabs 28, 28a in the direction indicated by arrows "E" in FIGS. 10 and 11 from a position secured only to the first vial and cap assembly 2 (FIG. 9), to a position secured to both the first and second vial and cap assemblies 2, 2a (FIG. 10), and to a position secured only to the second vial and cap assembly 2a (FIG. 11). Each of the cap assemblies 2, 2a may include a bump or a protrusion (not shown) at an outside edge diametrically opposite of their respective tunnels 32, 32a, which prevent the identification tag 100 from sliding off beyond the edge of the cap assemblies 2, 2a as the tag 100 is being moved.

Fruit flies are used in molecular, genetic and cell biological research, which necessitates maintenance of large genetically defined stocks of fruit flies. The fruit flies are typically maintained in vials that have food media in the bottom of the vial. To maintain stocks of fruit flies, the fruit flies must be transferred to new vials with food media every 10 to 20 days. The disclosed vial and cap assemblies 2, 2a facilitate maintenance of cultures of fruit flies and other insects in an efficient manner while preventing stock contamination, insect loss, and misidentification of the cultures.

In order to transfer fruit flies from the first vial and cap assembly 2 to the second vial and cap assembly 2a, the second vial and cap assembly 2a (in the closed position) is coupled to the first vial and cap assembly 2 (in the closed position) by positioning the flat surface 34a of the second vial cap 12a against the flat surface 34 of the first vial cap 12 and rotating the second vial and cap assembly 2a in relation to the first vial and cap assembly 2 to move the connectors 40a on the second vial cap 12a into engagement with the connectors 40 on the first vial cap 12 as described above (see FIGS. 7-7C).

Once the second vial and cap assembly 2a is coupled to the first vial and cap assembly 2, the vial caps 12, 12a can be moved upwardly to the open position to move the tunnels 32, 32a above the open ends 15, 15a of the vials 10, 10a as shown in FIG. 8. Moving the vial caps 12, 12a upward, provides a channel that allows the fruit flies to move from the first vial 10 into the second vial 10a to access the food media 18 in the second vial 10a. After the fruit flies have moved from the first vial 10 into the second vial 10a, the vial caps 12, 12a can be moved from the open positions back to the closed positions, and the first vial and cap assembly 2 can be uncoupled from the second vial and cap assembly 2a. This process can be repeated every 10 to 20 days to maintain the cultures of fruit flies without any danger of the fruit flies escaping into the environment or contamination of the culture.

The diametrically opposed tabs 28, 28a on the outer surfaces 26, 26a of the vial caps 12, 12a allow the identification tag 100 on the outer surfaces 26, 26a of the vial caps 12, 12a to be transferred from the first vial and cap assembly 2 to the second vial and cap assembly 2a without ever removing the identification tag 100 from the first and second vial and cap assemblies 2, 2a. This minimizes any likelihood that the insect cultures contained within the first and second vials 10, 10a will be incorrectly labeled or identified.

In certain aspects of the disclosure, the vial caps 12, 12a are positioned at the upper end of the vials 10, 10a such that when the vial caps 12, 12a are in the open positions, the fruit flies or insects can travel upwardly within cavity of the first vial 10 and pass through the tunnels 32, 32a into the cavity 16a of the second vial 10a. However, it is also envisioned that the first and second vial and cap assemblies can be inverted, and the food media can be received within the vial caps 12, 12a. When positioned in this manner, the insect larva will burrow through the food media and travel through the tunnels 32, 32a from the cavity 16 of the first vial 10 into the cavity 16a of the second vial 10a.

In certain embodiments, the vial caps may have additional structural elements that open and close the tunnels during coupling. The vial caps may have a folded-in spring, which may be formed by injection molded from a suitable polymer. The spring may be attached inside the vial via a living hinge by injection molding the spring along with the vial cap. It is also envisioned that the spring and the vial cap may be formed separately and that the spring is then inserted inside the vial. The spring is movable from an expanded state to a compressed state inside the vial cap. In the expanded the state the spring presses against the tunnel thereby sealing the tunnel. And in the compressed state the spring is spaced away from the tunnel thereby opening the tunnel. The spring may be actuated by a pin coupled to the spring and extending through an opening in the side wall of the vial cap, and in particular through the flat surface beside the tunnel. When pressed into the vial cap, the pin compresses the spring. Thus, when two vial caps are joined, the flat surfaces of each vial cap push against the pin of the opposite cap thereby opening the tunnel. The pin may have any suitable cross-sectional shape, e.g., circular, rectangular, etc. to achieve even distribution of force by the opposing vial cap on the pin. This embodiment of the vial cap is intended to be seated on the vial and is opened during coupling with an opposing vial cap, thus obviating the need for raising the vial cap to unseal the tunnel and lowering the vial cap to seal the vial. This design also avoids accidentally closing or opening tunnels. In addition, the design allows the capped vials to be stacked in boxes.

In another embodiment, a twisting cap is also envisioned. The vial cap includes two portions—a stationary portion that is seated on the vial and a slider movable relative to the stationary portion, which is movable from a closed position in which the slider covers the tunnel and an open position in which the tunnel is unsealed. This design also allows for stacking boxes of vials.

In a further embodiment, the vial caps may be configured to fit inside the vials. The internally seated vial cap includes one or more snapping clips that are configured to engage the annular rib of the vial to secure the vial cap to the vial, with a portion of the vial cap frictionally fitting inside the vial. The clips may be positioned above the tunnel, such that the tunnel is opened and closed in the manner described above, i.e., by raising and lowering the vial cap and the tunnel into and out of the vial. The clips may be positioned below the tunnel and the spring described above may be incorporated into the internally seated vial cap with the pin being used to seal and unseal the tunnel.

Figure 12:
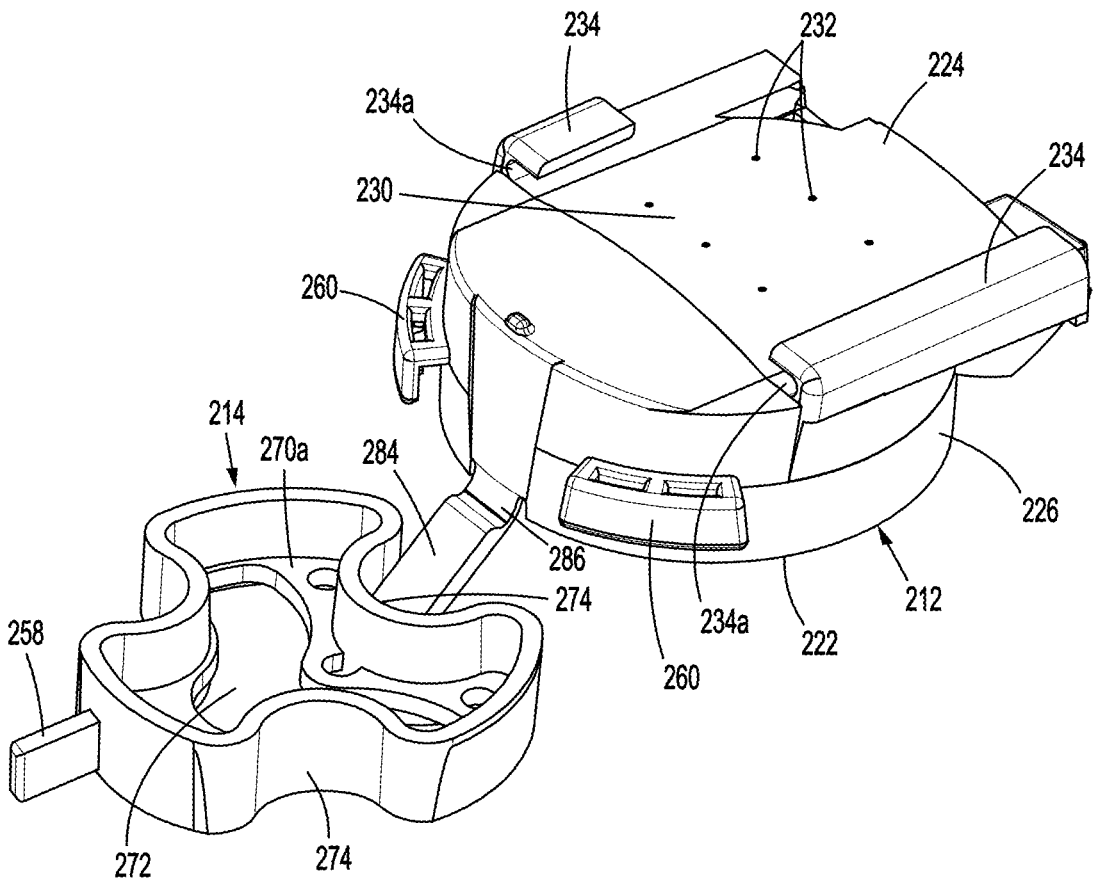
FIG. 12 is a side, perspective, top view of another embodiment of a first vial cap and a first cap valve in a disassembled configuration.
Figure 12A:
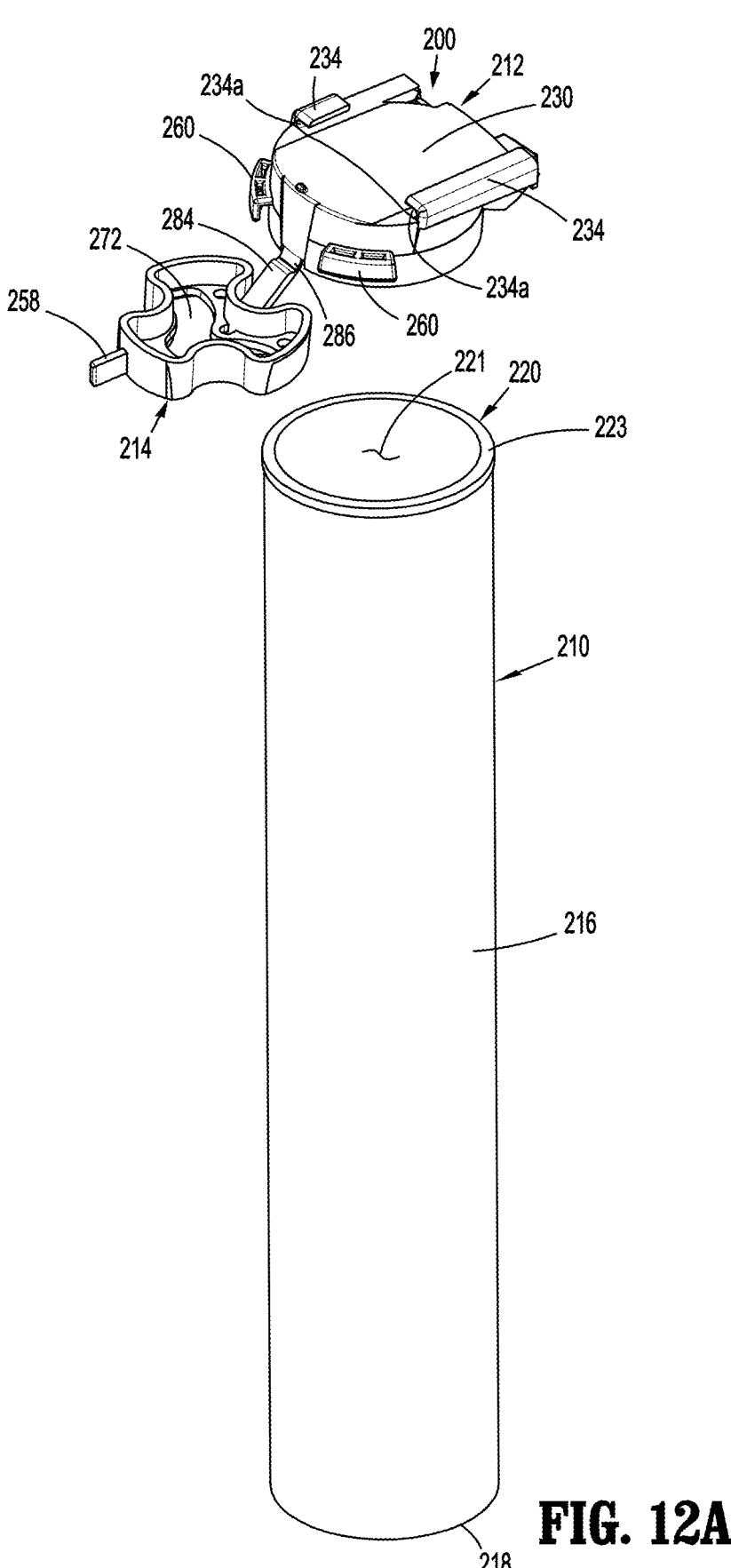
FIG. 12A is a side, perspective, top view of the first vial cap and the first cap valve of FIG. 12 separated from a first vial of a first vial cap assembly according to an embodiment of the present disclosure.
Figure 13:
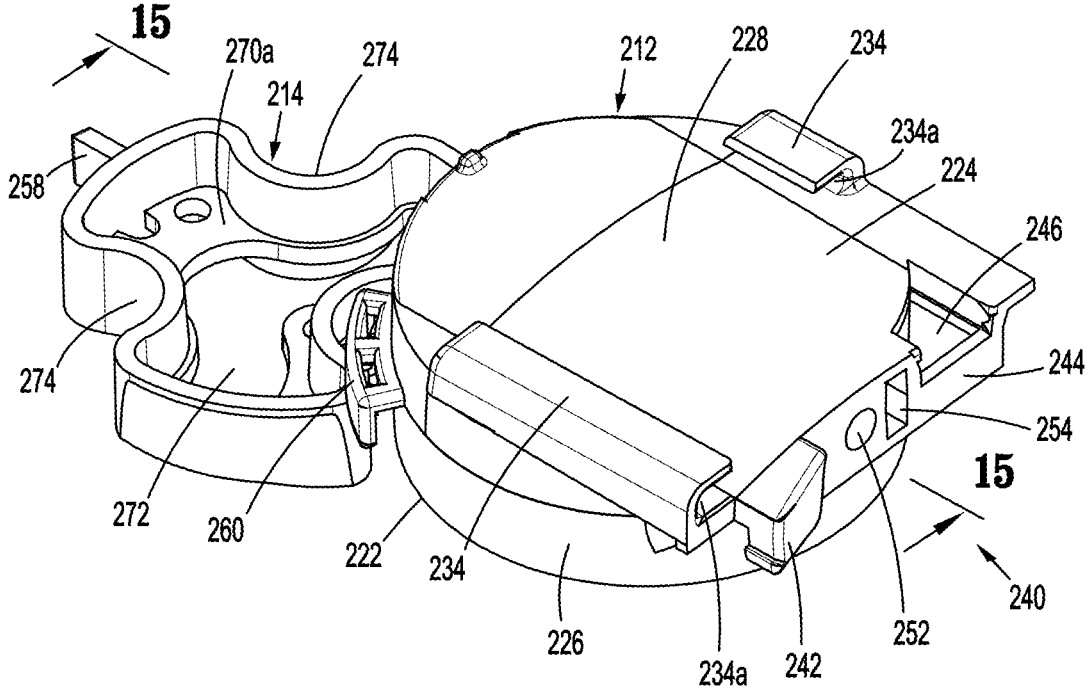
FIG. 13 is an alternate, side, perspective, top view of the first vial cap and the first cap valve of FIG. 12 in the disassembled configuration.
Figure 14:
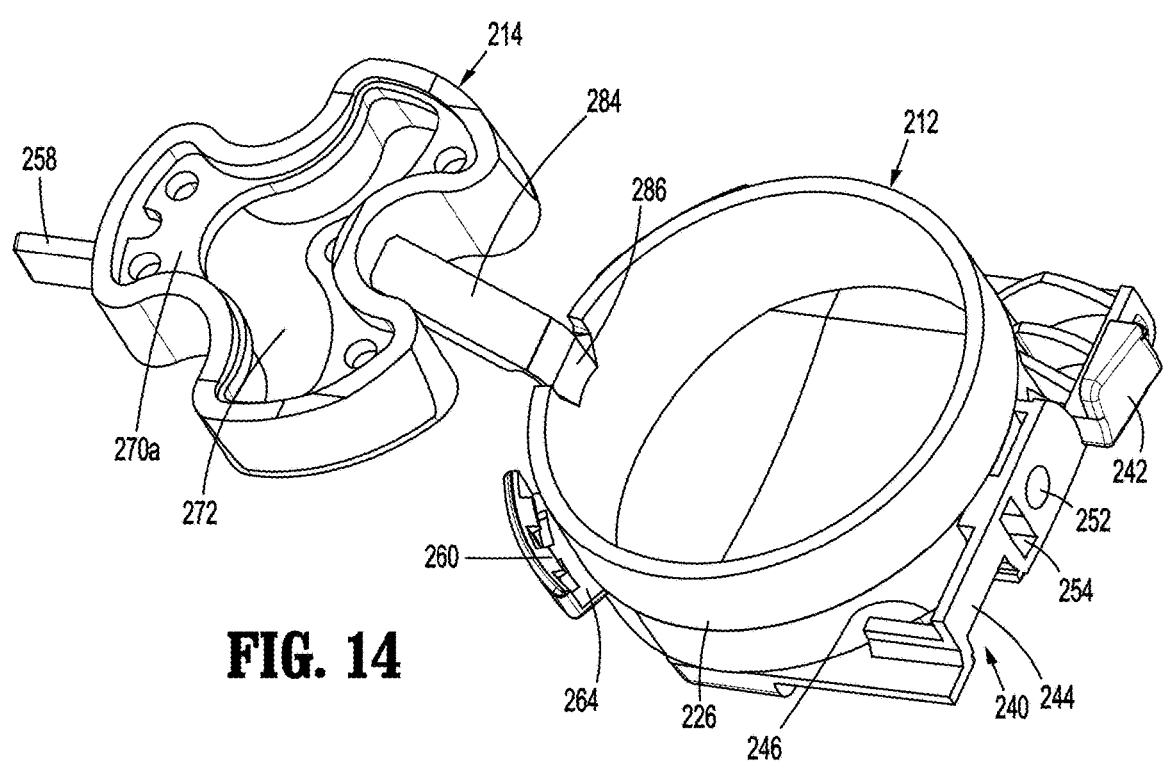
FIG. 14 is a side, perspective, bottom view of the first vial cap and the first cap valve of FIG. 12 in the disassembled configuration.
Figure 15:
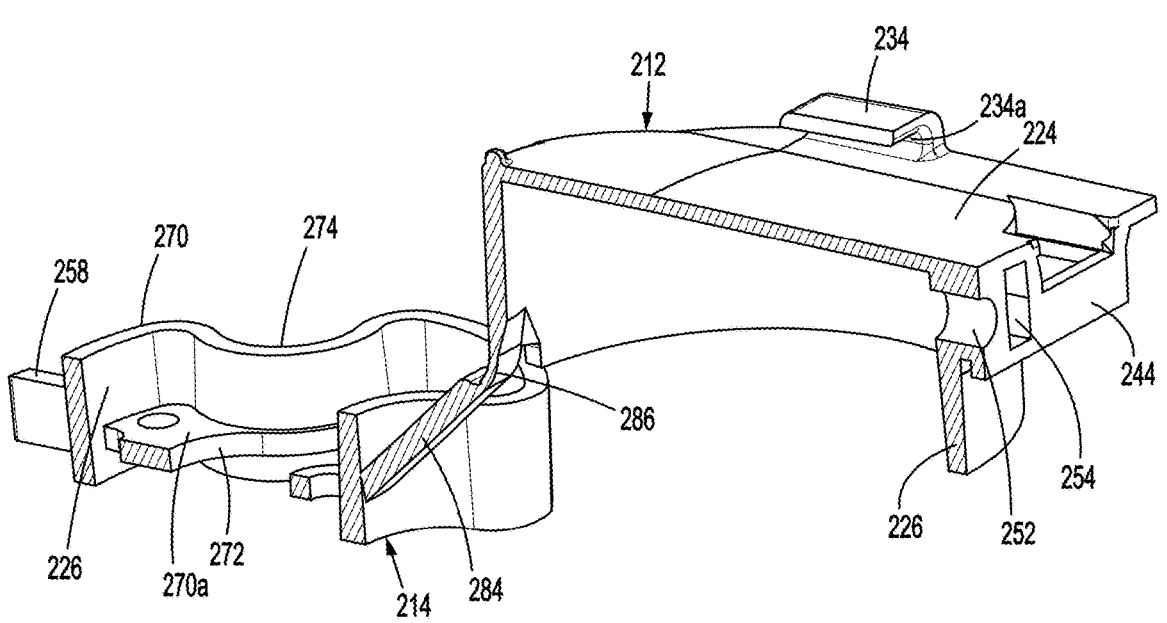
FIG. 15 is a cross-sectional view of the first vial cap and the first cap valve in the dissembled configuration taken along section line 15-15 of FIG. 13.
Figure 16:
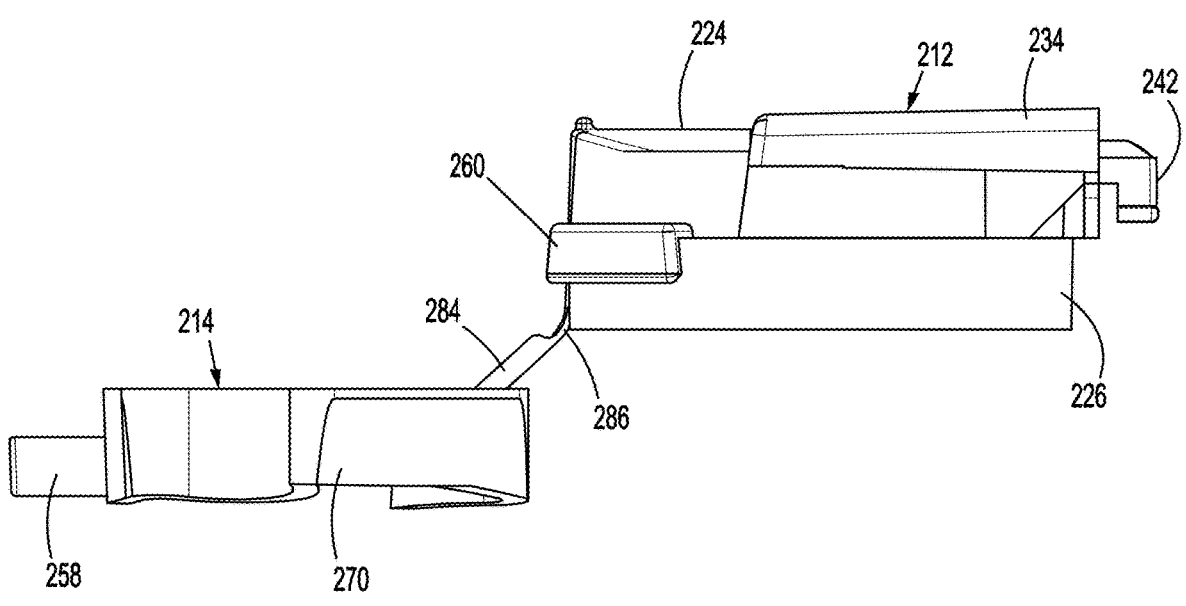
FIG. 16 is a side view of the first vial cap and the first cap valve of FIG. 12 with the first vial cap and the first cap valve in the disassembled configuration.
Figure 17:
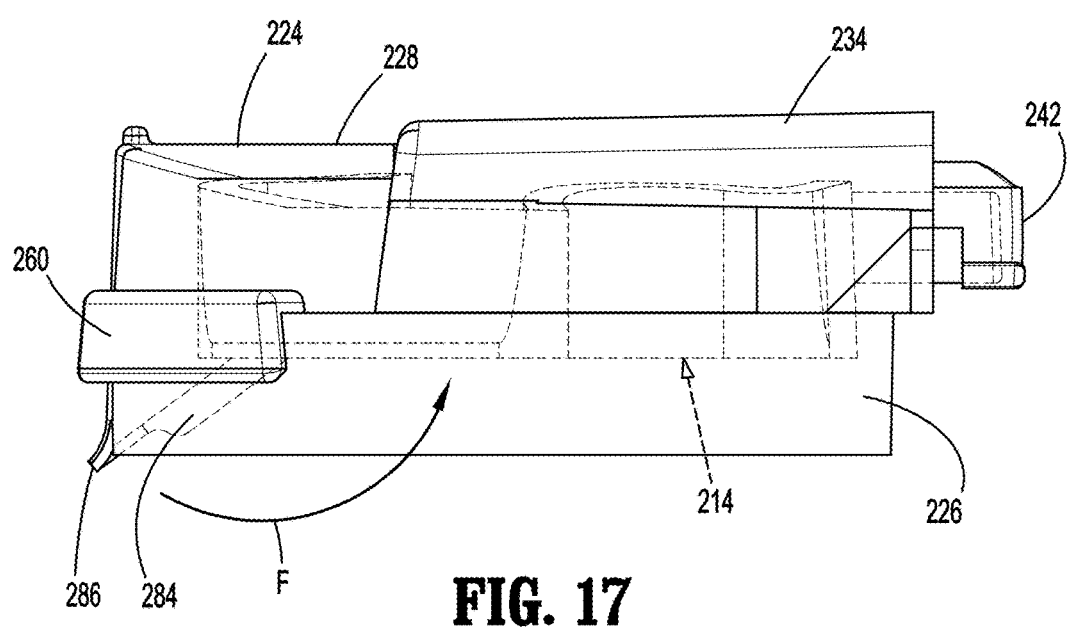
FIG. 17 is a side view of the first vial cap and the first cap valve of FIG. 12 with the first vial cap and the first cap valve in an assembled configuration.
Figure 18:
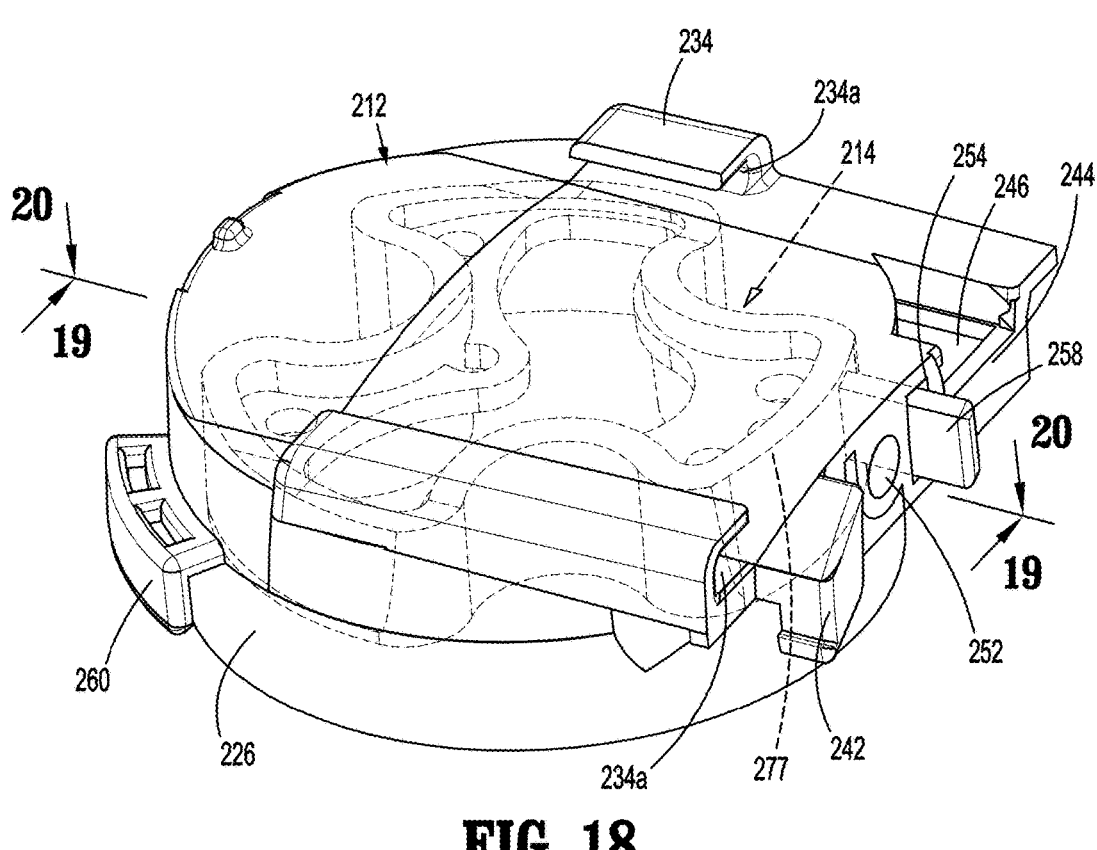
FIG. 18 is a side, perspective, top view of the first vial cap and the first cap valve (shown in phantom) of FIG. 12 in the assembled configuration.
Figure 19:
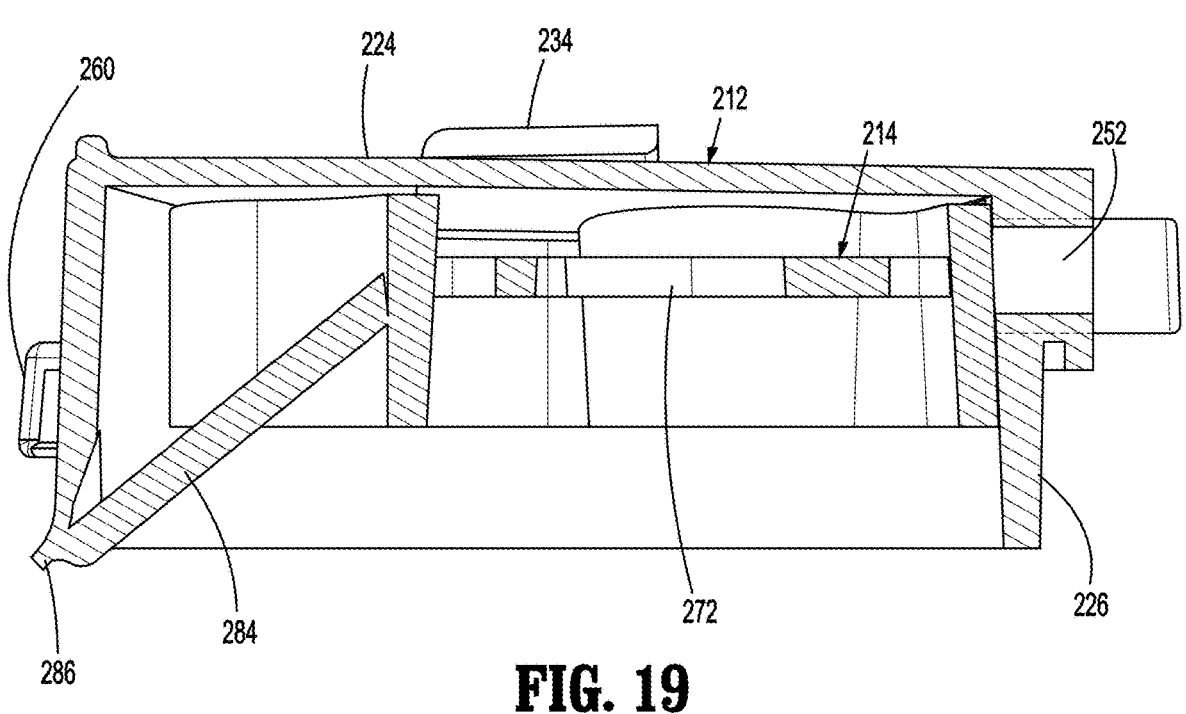
FIG. 19 is a cross-sectional view of the first vial cap and the first cap valve in the assembled configuration taken along section line 19-19 of FIG. 18.
Figures 20, 21:
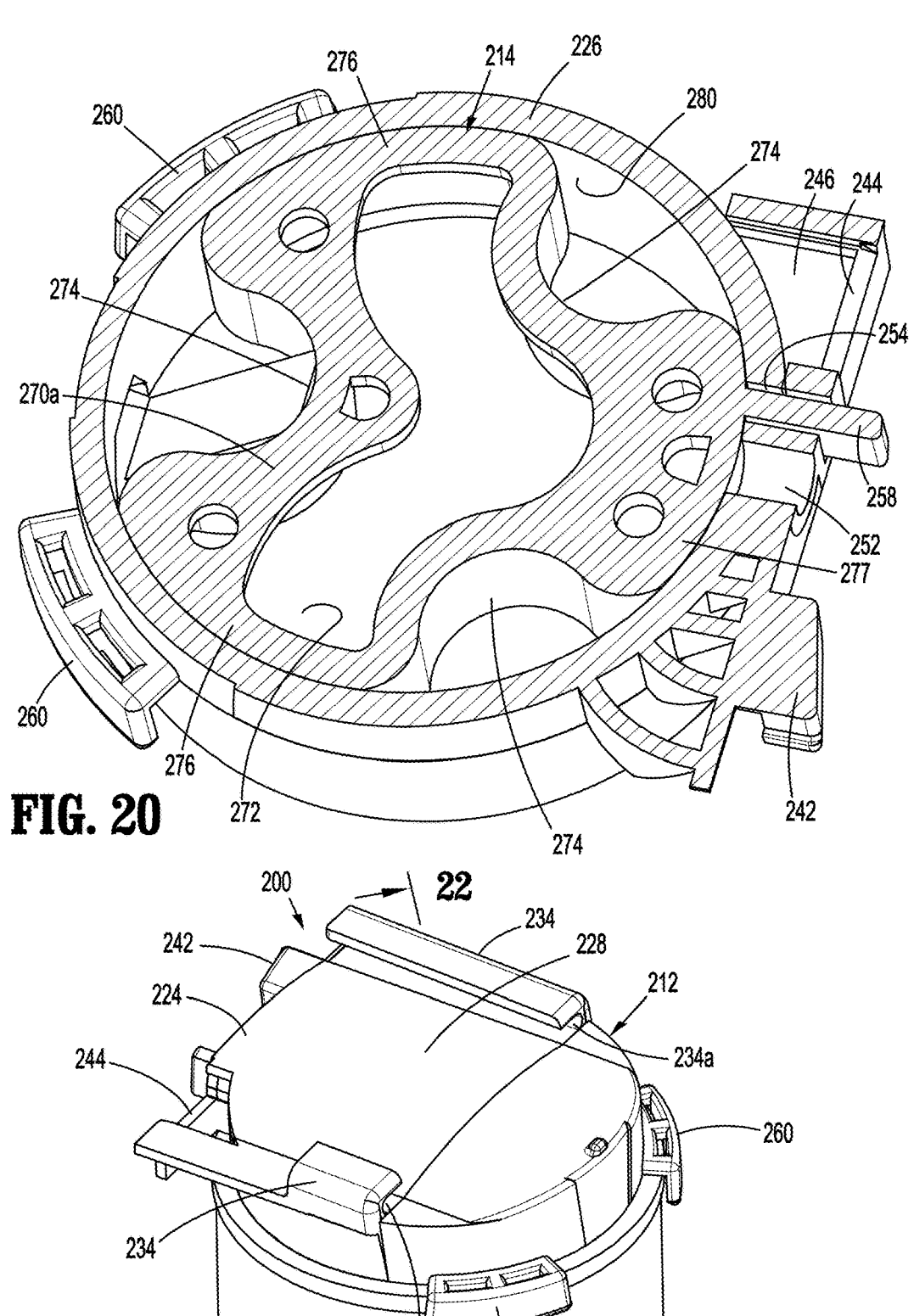
FIG. 20 is a cross-sectional view of the first vial cap and the first cap valve in the assembled configuration taken along section line 20-20 of FIG. 18.
FIG. 21 is a side, perspective, top view of the first vial cap coupled to the first vial of the first vial cap assembly.
Figure 22:
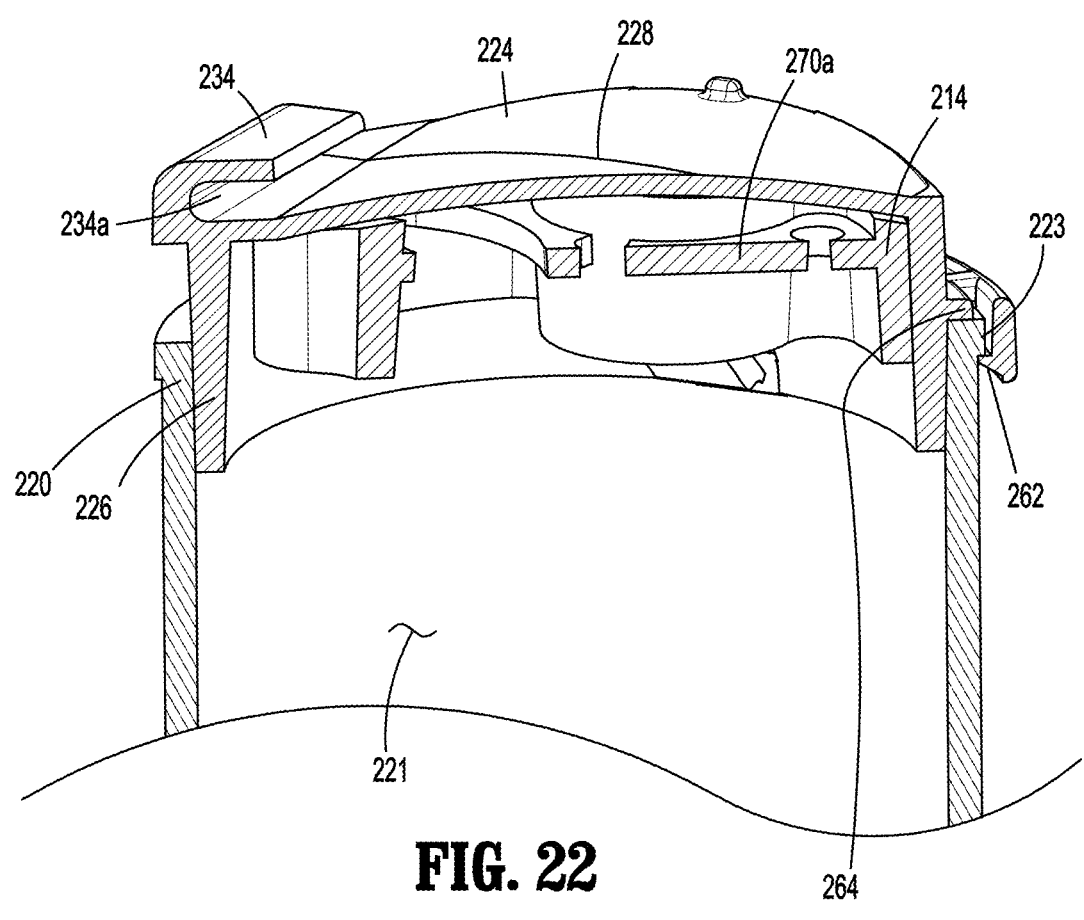
FIG. 22 is a cross-sectional view of the first vial cap assembly taken along section line 22-22 of FIG. 21 with the first cap valve in a closed position.
Figure 23:
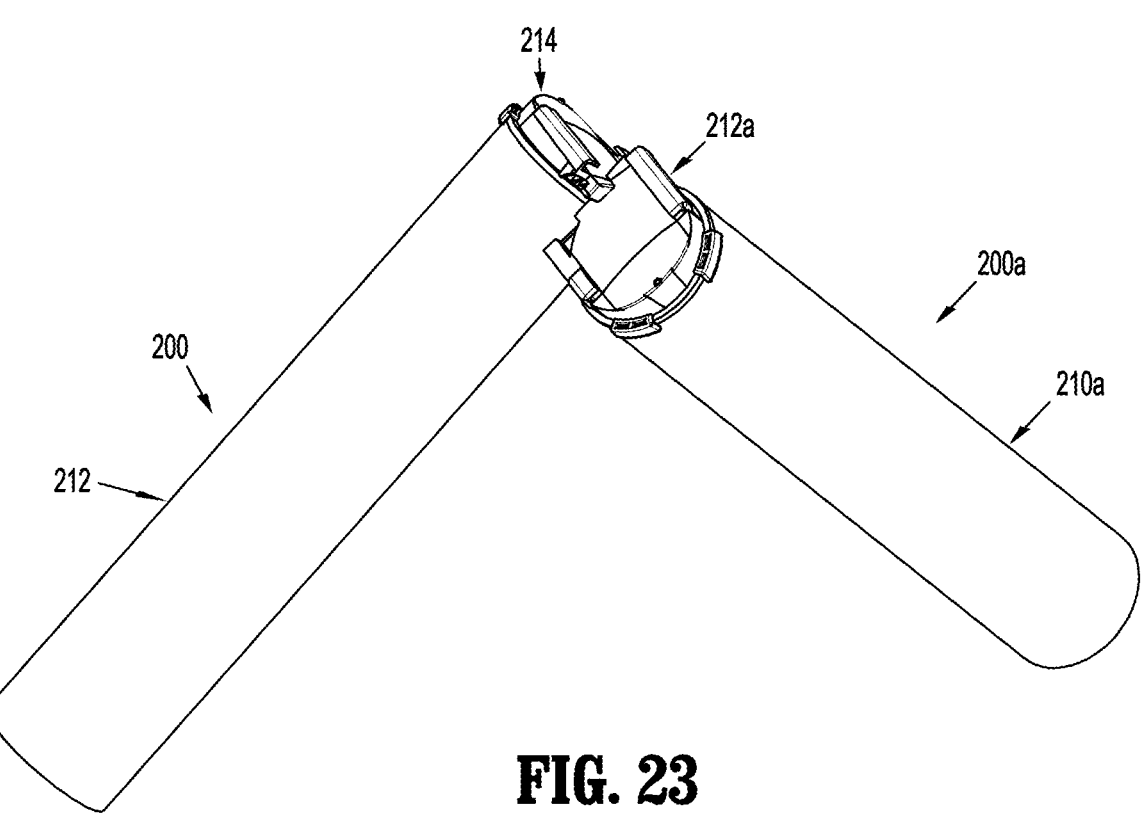
FIG. 23 is a side, perspective view of the first vial cap being coupled to a second vial cap of a second vial cap assembly being coupled to each other.
Figure 24:
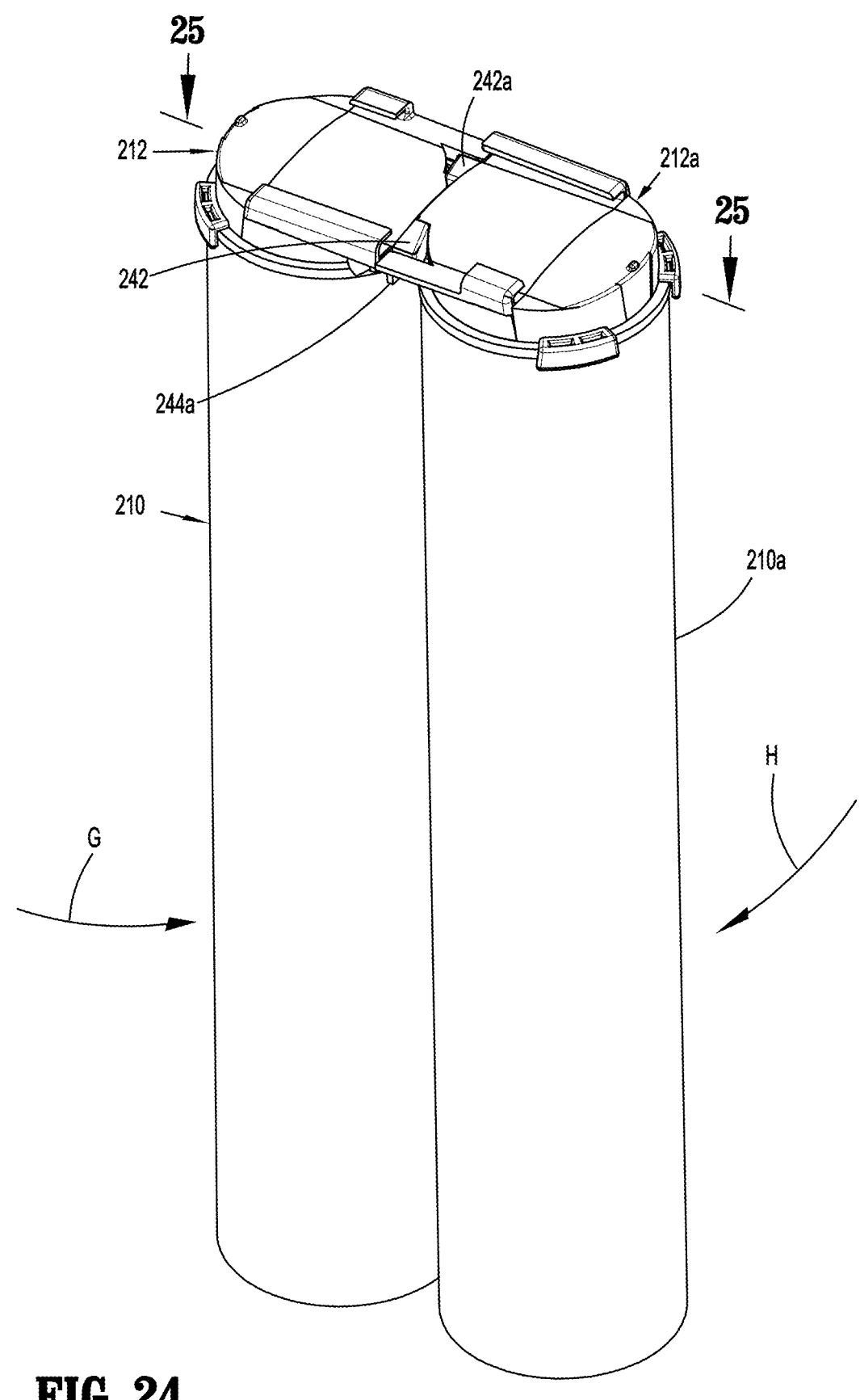
FIG. 24 is a side, perspective view of the first vial cap assembly coupled to the second vial cap assembly.
Figure 25:
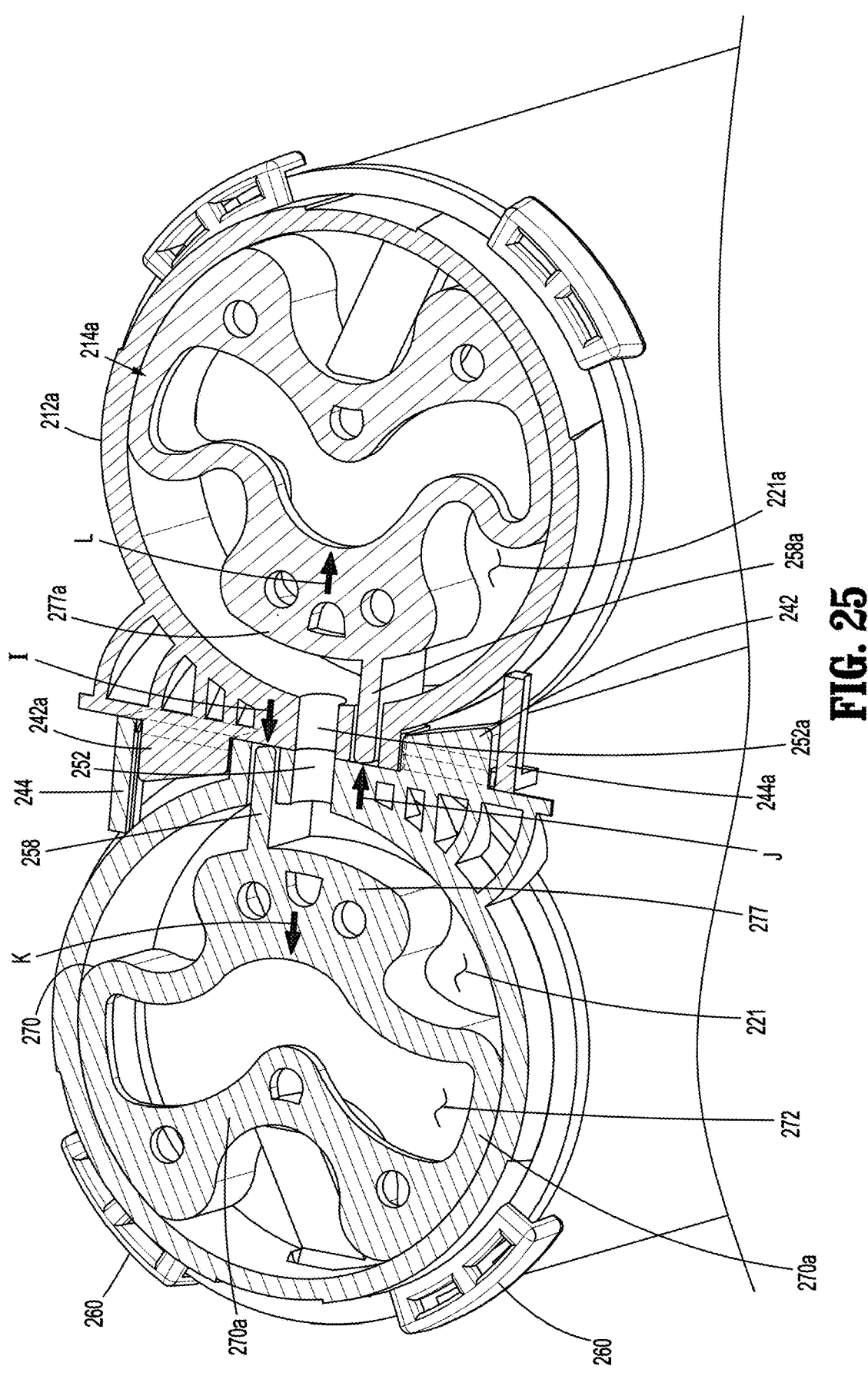
FIG. 25 is a cross-sectional view of the coupled first vial cap assembly and the second vial cap assembly taken along section line 25-25 of FIG. 24 illustrating the first cap valve and a second cap valve in an open position.

FIGS. 12-22 illustrate another embodiment of the first vial and cap assembly shown generally as first vial and cap assembly 200 (FIGS. 12A and 21). The first vial and cap assembly 200 is releasably couplable with an identical, second vial and cap assembly 200a as shown in FIGS. 23-25. With reference to FIGS. 12-14, the first vial and cap assembly 200 includes a first vial 210, a first vial cap 212, and a first cap valve 214. The first vial 210 is illustrated as having a cylindrical body 216 with a closed end 218 and an open end 220 that defines an opening that provides access to a cavity 221 defined by the first vial 210. It is envisioned that the body 216 of the first vial 210 can have a variety of configurations including square, rectangular, hexagonal, octagonal, oval, or the like. The upper portion of the first vial 210 includes an annular or semi-annular rib 223 that extends about the open end 220 of the first vial 210. As described above regarding the first vial cap assembly 2 (FIG. 1), the first vial and cap assembly 200 forms a part of a system for maintaining cultures of fruit flies and other insects.

FIGS. 12-15 illustrate the first vial cap 212 which includes a body 222 having a top wall 224 and a side wall 226 that extends downwardly from the top wall 224. The first vial cap 212 is configured to be received within the open end 220 of the first vial 210 (FIG. 21) and may have a thickness that decreases as the side wall 226 extends away from the top wall 224. In aspects of the disclosure, the top wall 224 of the first vial cap 212 includes an outer surface 228 that is angled or sloped upwardly from outer edges of the first vial cap 212 towards a midline of the first vial cap 212 to define a ridge, peak, dome shape, or raised surface at a central location on the first vial cap 212. The top wall 224 may also have one or more air openings 232 (FIG. 12) that are sized to prevent escape of the insects held in the first vial 210 while allowing for gas exchange between the atmosphere and the cavity 221 of the first vial 210.

The top wall 224 of the first vial cap 212 supports diametrically disposed tabs 234 that are positioned on opposite sides of the top wall 224. The raised surface on the outer surface 228 of the top wall 224 is positioned between the tabs 234. The tabs 234 have L-shaped configurations and include overhangs that extend over the outer surface 228 of the top wall 224 of the first vial cap 212. The tabs 234 are provided to secure the identification tag 100 (FIG. 10) to the first vial cap 212. More specifically, the tabs 234 define channels 234a that slidably receive the identification tag 100 to allow the identification tag 100 to slide onto and off the outer surface 228 of the top wall 224 of the first vial cap 212. The raised surface on the outer surface 228 of the top wall 224 increases frictional engagement between the top wall 224 of the first vial cap 212 and a bottom surface of the identification tag 100 to better secure the identification tag 100 to the first vial cap 212. The tabs 234 may extend along the entire length of the first vial cap 212 or along only a portion of the length of the first vial cap 212. In some aspects of the disclosure, the lengths of the diametrically opposed tabs 234 can be different from each other. In certain aspects of the disclosure, the tabs 234 extend outwardly of the circumference of the top wall 224 of the first vial cap 212.

The first vial cap 212 includes cap connectors 240 that depend from the side wall 226 of the first vial cap 212. In aspects of the disclosure, the connectors 240 are configured to engage connectors 240a of a second vial cap 212a (FIG. 24) to releasably secure the first and second vial caps 212, 212a together. In certain aspects of the disclosure, the connectors 240 are bayonet appendages that can be rotated into engagement with respective female connectors 244a of the second vial cap 212a to secure the first and second vial caps 212, 212a together. In certain aspects of the disclosure, the connectors 240 include a male connector 242 and a female connector 244, and the female connector 244 defines an opening 246 (FIG. 13) that receives the male connector 242a (FIG. 25) when the first vial cap 212 is rotatably engaged with the second vial cap 212a (FIG. 24).

It is envisioned that the connectors 240, 240a of the first and second vial caps 212, 212a can have a variety of different configurations capable of releasably securing the first and second vial caps 212, 212a together as shown in FIGS. 23-25. For example, the connectors 240, 240a can include interlocking features, e.g., dove-tail connectors, to secure the vial caps 212, 212a together. It is noted that if the connectors 240, 240a are dove-tail connectors, the connectors 240, 240a would slide linearly in relation to each other to secure the first and second vial caps 212, 212a together.

FIG. 13 illustrates the side wall 226 of the first vial cap 212 with the connectors 240 which includes a flat surface 250 that is positioned between the male connector 242 and the female connector 244 and defines a tunnel 252 and a through bore 254 that pass through the flat surface 250. The flat surface 250 orients and positions the first vial cap 212 in relation to the second vial cap 212a (FIG. 23) that is to be coupled to the first vial cap 212 to align the tunnel 252 of the first vial cap 212 with a tunnel 252a of the second vial cap 212a (FIG. 25) when the first and second vial caps 212, 212a are coupled together. The through bore 254 receives an abutment member 258 of the first cap valve 214 as described in further detail below.

The first vial cap 212 may also include gripping members 260 that extend outwardly from the side wall 226 of the first vial cap 212 at a position spaced from the top wall 224 and engage the rib 223 of the first vial 210 when the first vial cap 212 is coupled to the first vial 210. The gripping members 260 may be formed from a resilient material and include detents 262 (FIG. 22) that pass over the rib 223 and engage an undersurface of the rib 223 when the first vial cap 212 is secured to the first vial 210. In some aspects of the disclosure, the gripping members 260 include an inner stop surface 264 (FIG. 22) that engage an upper end of the first vial 212 when the vial cap 212 is fully inserted into the open end 220 of the first vial 210 to limit further insertion of the side wall 226 of the first vial cap 212 into the first vial 210.

FIGS. 12-22 illustrate the first cap valve 214 which includes a body 270 that is formed from a resilient material and is received within the first vial cap 212. The body 270 may be formed from a plurality of leaf springs or any other flexible structures that allow for the body 270 to be compressed.

The body 270 supports the abutment member 258 of the first cap valve 214 and defines an opening 272 that extends through the body 270. The body 270 can include a rib 270a that defines the opening 272 and provides rigidity to the body 270. In aspects of the disclosure, the body 270 may have a plurality of interconnected petal-like configuration that defines concavities 274 that are positioned about the body 270. The concavities 274 allow the body 270 to compress inwardly to be received within the first vial cap 212 in the first (i.e., partially) compressed state (FIG. 20). In the first compressed state, portions 276 of the body 270 between the concavities 274 frictionally engage an inner surface 280 of the side wall 226 of the first vial cap 212. One of the seal portions 277 seals the tunnel 252 defined in the side wall 226 of the first vial cap 212 when the body 270 is in the first state. When the first cap valve 214 is received within the first vial cap 212, the abutment member 258 of the first cap valve 214 extends through the through bore 254 of the first vial cap 212 to a position outwardly of the flat surface 250 of the first vial cap 212. In aspects of the disclosure, the abutment member 258 may be in the form of a finger that extends outwardly from the body 270 through the through bore 254 of the first vial cap 212. While the body 270 is in the first compressed state, the first cap valve 214 is in a sealed state, in which the tunnel 252 is sealed by a portion of the body 270.

As the abutment member 258 is engaged, as described below, the body 270 is further compressed (i.e., to a second compressed state) when the abutment member 258. Thus, in the first compressed state the body 270 is less compressed than in the second compressed state. While the body 270 is in the second compressed state, the first valve cap 214 is in an unsealed state, in which the body 270 is spaced apart from the side wall 226 of the first vial cap 212 and the tunnel 252 is open.

The first vial cap 212 and the first cap valve 214 can be integrally formed. In certain aspects of the disclosure, the first vial cap 212 may be optionally coupled to the first cap valve 214 by a link or tether 284 that includes a first end that is coupled to the first vial cap 212 by a living hinge 286 and a second end that is secured to the first cap valve 214. As the first cap valve 214 is positioned within the first vial cap 212, the first cap valve 214 is pivoted about the living hinge 286 in the direction indicated by arrow "F" in FIG. 17 into the cavity defined by the first vial cap 212. To position the abutment member 258 of the first cap valve 212 into the through bore 254 of the first vial cap 212, the body 270 of the first cap valve 214 is compressed as the first cap valve 214 is positioned into the cavity defined by the first vial cap 212. Once the abutment member 258 is aligned with the through bore 254, the body 270 of the first cap valve 214 is released and allowed to return to a non-deformed or slightly deformed state in which the seal portion 277 of the body 270 of the first cap valve 214 engages the inner surface 280 of the side wall 226 of the first vial cap 212 to seal the tunnel 252.

It is envisioned that the first cap valve 214 and the first vial cap 212 can be formed separately and need not be connected by the tether 284. It is also envisioned that the first cap valve 212 can have a variety of different configurations and need not have a clover-like shape. More specifically, the first cap valve 214 can have any configuration capable of releasably sealing the tunnel 252 of the first vial cap 212.

FIGS. 23-25 illustrate the first vial and cap assembly 200 as the first vial and cap assembly 200 is coupled to the second vial and cap assembly 200a. The second vial and cap assembly 200a is identical to the first vial and cap assembly 200 and includes a second vial 210a, a second vial cap 212a, and a second cap valve 214a (FIG. 25). When the first vial cap 212 is secured to the first vial 210 and the second vial cap 212a is secured to the second vial 210a, the first cap valve 214 seals the tunnel 252 (FIG. 20) in the first vial cap 212 and the second cap valve 214a seals the tunnel 252a (FIG. 25) in the second vial cap 212a as described above. To connect the first vial and cap assembly 200 to the second vial cap assembly, the flat surface 250 of the first vial and cap assembly 200 is pressed against the flat surface 250a of the second vial and cap assembly 200a and the first and second vial and cap assemblies 200, 200a are rotated in relation to each other in the directions indicated by arrows "G" and "H" in FIG. 24 to move the male connector 242 of the first vial cap 212 into engagement with the female connector 244a of the second vial cap 212a and to move the male connector 242a of the second vial cap 212a into engagement with the female connector 244 of the first vial cap 212. When the flat surfaces 250, 250a are pressed together prior to rotation of the assemblies 200 and 200a relative to each other, the abutment members 258, 258a of the first and second cap valves 214, 214a are pressed inwardly in the directions indicated by arrows "I" and "J" in FIG. 25 by the flat surface 250, 250a of the other vial cap 212, 212a. As the abutment members 258, 258a are moved, the seal portions 276, 276a of the first and second cap valves 214, 214a are moved in the direction indicated by arrows "K" and "L" in FIG. 25 to unseal the tunnels 252, 252a in the first and second vial caps 212, 212a. When the tunnels 252, 252a are unsealed, the cavity 221 of the first vial 210 is in communication with the cavity 221a in the second vial 210a. As such, the tunnels 252, 252a are unsealed as the first vial and cap assembly 200 is coupled to the second vial and cap assembly 200a in this manner.

It is envisioned that the abutment members 258, 258a of the first and second cap valves 214, 214a could be configured such that rotational movement of the first vial cap 212 in relation to the second vial cap 212a effects inward movement of the abutment members 258, 258a to move the cap valves 214, 214a from an unsealed state to a sealed state.

The abutment members 258, 258a may include angled cam surfaces (not shown) that that are positioned to engage the first and second vial caps 212, 212a as the first and second vial caps 212, 212a are rotatably coupled together to cam the abutment members 258, 258a inwardly and unseal the tunnels 252, 252a.

As described above, the vial caps 212, 212a are positioned at the upper end of the vials 210, 210a such that when the vial cap valves 214, 214a are in the open or unsealed states, fruit flies or insects can travel upwardly within cavity 221 of the first vial 210 and pass through the tunnels 252, 252a into the cavity 221a of the second vial 210a.

It will be appreciated that of the above-disclosed and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the following claims. Unless specifically recited in a claim, steps, or components according to claims should not be implied or imported from the specification or any other claims as to any particular order, number, position, size, shape, angle, or material.

What is claimed is:

1. An insect culture maintenance system comprising:
a first cap having a top wall and a side wall extending downwardly from the top wall, the top wall and the side wall of the first cap defining a first cavity configured to receive an open end of a first vial, the side wall of the first cap defining a first tunnel and supporting a first connector, the first tunnel extending through the side wall of the first cap; and
a second cap having a top wall and a side wall extending downwardly from the top wall, the side wall of the second cap defining a second cavity configured to receive an open end of a second vial, the side wall of the second cap defining a second tunnel that extends through the side wall of the second cap, the side wall of the second cap supporting a second connector,
wherein the first connector is couplable to the second connector to releasably secure the side wall of the first cap into connectable abutting engagement with the side wall of the second cap such that the first tunnel communicates with the second tunnel to allow passage between the first cavity of the first cap and the second cavity of the second cap.

2. The insect culture maintenance system of claim 1, wherein the side wall of each of the first cap and second cap includes an inwardly extending rib.

3. The insect culture maintenance system of claim 1, wherein the top wall of each of the first cap and the second cap includes diametrically opposed tabs, each of the diametrically opposed tabs having an overhang that extends over the top wall of the respective first or second cap, the diametrically opposed tabs configured to retain a slidable identification tag on at least one of the first cap or the second cap.

4. The insect culture maintenance system of claim 3, wherein the top wall of each of the first cap and the second cap has a raised outer surface.

5. The insect culture maintenance system of claim 1, wherein the first connector includes a first bayonet appendage and a second bayonet appendage positioned on opposite sides of the first tunnel, and the second connector includes a third bayonet appendage and a fourth bayonet appendage positioned on opposite sides of the second tunnel, the first and second bayonet appendages configured to rotatably engage with the third and fourth bayonet appendages to couple the first cap to the second cap.

6. The insect culture maintenance system of claim 5, wherein the side walls of each of the first cap and the second cap include a flat surface positioned about the first tunnel and the second tunnel, respectively.

7. The insect culture maintenance system of claim 1, further including food media positioned within the first and second vials.

8. A vial cap for insect culture maintenance comprising:
a top wall and a side wall extending about the top wall and defining a cap cavity configured to receive an open end of a vial such that the vial cap is slidable along an outer surface of the vial between a closed position and an open position, the side wall defining a tunnel that extends through the side wall, the tunnel being sealed by the vial when the vial cap is in the closed position and unobstructed by the vial when the vial cap is in the open position; and
a connector supported on the side wall, the connector configured to couple the vial cap to a second vial cap wherein the connector includes a first bayonet appendage and a second bayonet appendage positioned on opposite sides of the tunnel.

9. The vial cap of claim 8, wherein the side wall includes an inwardly extending rib configured to engage an outwardly extending rib of the vial when the vial cap is in the open position to releasably retain the vial cap on the vial.

10. The vial cap of claim 8, wherein the top wall includes diametrically opposed tabs, each of the diametrically opposed tabs having an overhang that extends over the top wall, the diametrically opposed tabs configured to retain a slidable identification tag on the vial cap.

11. The vial cap of claim 10, wherein the top wall has a raised outer surface that is angled upwardly from side edges towards a center of the top wall.

12. The vial cap of claim 8, wherein the side wall includes a flat surface positioned about the tunnel.

13. An insect culture maintenance system comprising:
a cap having a top wall and a side wall extending downwardly from the top wall, the top wall and the side wall defining a first cavity, the side wall defining a tunnel and a through bore that extend through the side wall; and
a cap valve having a body and including an abutment member extending outwardly from the body through the through bore of the cap, the body of the cap valve movable from a first state to a second state in response to inward movement of the abutment member within the through bore of the cap, wherein in the first state, the cap valve seals the tunnel, and in the second state, the cap valve unseals the tunnel.

14. The insect culture maintenance system of claim 13, further including a vial having an outer surface, a closed end, and an open end, the vial defining a second cavity, the open end of the vial defining an opening that provides access to the second cavity.

15. The insect culture maintenance system of claim 14, wherein the side wall of the cap is received within the open end of the vial.

16. The insect culture maintenance system of claim 14, wherein the side wall of the cap supports gripping members positioned to engage the outer surface of the vial to secure the cap to the vial.

17. The insect culture maintenance system of claim 16, wherein the vial includes a rib that is positioned adjacent the open end of the vial, and the gripping members include detents that engage the rib.

18. The insect culture maintenance system of claim 13, wherein the body of the cap valve is formed from a resilient material, and the side wall of the cap includes an inner surface, the cap valve having a seal portion that is engaged with the inner surface of the side wall of the cap to seal the tunnel when the cap valve is in the first state.

19. The insect culture maintenance system of claim 18, wherein the inward movement of the abutment member within the through bore of the cap deforms the body of the cap valve to move the seal portion of the cap valve away from the inner surface of the side wall of the cap to unseal the tunnel.

20. The insect culture maintenance system of claim 13, wherein the top wall supports diametrically opposed tabs, each of the diametrically opposed tabs having an overhang that extends over the top wall, the diametrically opposed tabs configured to retain a slidable identification tag on the cap.

21. An insect culture maintenance system comprising:
a first cap assembly including:
a first cap having a top wall and a side wall extending downwardly from the top wall, the top wall and the side wall of the first cap defining a first cavity, the side wall of the first cap defining a first tunnel and a first through bore that extend through the side wall of the first cap, the side wall of the first cap having an outer surface supporting a first connector; and
a first cap valve having a body and including a first abutment member extending outwardly from the body through the first through bore of the first cap, the body of the first cap valve movable from a first state to a second state in response to inward movement of the abutment member within the first through bore of the cap, wherein in the first state, the first cap valve seals the first tunnel, and in the second state, the first cap valve unseals the first tunnel; and
a second cap assembly including:
a second cap having a top wall and a side wall extending downwardly from the top wall, the top wall and the side wall of the second cap defining a second cavity configured to receive an open end of a second vial, the side wall of the second cap defining a second tunnel and a second through bore that extend through the side wall of the second cap, the side wall of the second cap having an outer surface supporting a second connector; and
a second cap valve having a body and including a second abutment member extending outwardly from the body through the through bore of the second cap, the body of the second cap valve movable from a first state to a second state in response to inward movement of the second abutment member within the second through bore of the second cap, wherein in the first state of the second cap valve, the second cap valve seals the second tunnel, and in the second state of the second cap valve, the second cap valve unseals the second tunnel,
wherein the first connector is couplable to the second connector to secure the first cap to the second cap.

22. The insect culture maintenance system of claim 21, wherein the first cap is positioned to engage the second abutment member and the second cap is positioned to engage the first abutment member when the first connector is coupled to the second connector to move the first abutment member and the second abutment member inwardly within the first through bore and the second through bore.

23. The insect culture maintenance system of claim 22, further including a first vial and a second vial, each of the first vial and the second vial including an open end and a closed end, the first vial defining a third cavity and the second vial defining a fourth cavity, the first cap supported on the open end of the first vial and the second cap supported on the open end of the second vial.

24. The insect culture maintenance system of claim 23, wherein the side wall of the first cap is received within the third cavity of the first vial and the side wall of the second cap is received within the fourth cavity of the second vial.

25. The insect culture maintenance system of claim 24, wherein the bodies of the first cap valve and the second cap valve are formed from a resilient material, and the side walls of the first cap and the second cap include an inner surfaces, the first cap valve and the second cap valve having seal portions that are engaged with the inner surfaces of the side walls of the first cap and the second cap to seal the tunnels when the first cap valve and the second cap valve are in the first states.

26. The insect culture maintenance system of claim 25, wherein inward movements of the first abutment member and the second abutment member within the first through bore and the second through bore of the first cap and the second cap deforms the bodies of the first cap valve and the second cap valve to move the seal portions of the first cap valve and the second cap valve away from the inner surfaces of the side walls of the first cap and the second cap to unseal the first tunnel and the second tunnel.

27. The insect culture maintenance system of claim 23, wherein the side walls of the first cap and the second cap support gripping members positioned to engage the outer surfaces of the first vial and the second vial to secure the first cap and the second cap to the first vial and the second vial.

28. The insect culture maintenance system of claim 27, wherein each of the first vial and the second vial includes a rib that is positioned adjacent the open end of the first vial and the second vial, and the gripping members include detents that engage the ribs.

29. The insect culture maintenance system of claim 21, wherein the top walls of the first cap and the second cap support diametrically opposed tabs, each of the diametrically opposed tabs having an overhang that extends over the top wall, the diametrically opposed tabs configured to retain a slidable identification tag on the first cap and the second cap.

* * * * *